(12) United States Patent
Rogers et al.

(10) Patent No.: US 10,758,369 B2
(45) Date of Patent: Sep. 1, 2020

(54) EXPANDABLE AND ADJUSTABLE LORDOSIS INTERBODY FUSION SYSTEM

(71) Applicant: SPINEEX, INC., Fremont (CA)

(72) Inventors: Andrew Rogers, Sunnyvale, CA (US); Robyn Burrows-Ownbey, Hayward, CA (US)

(73) Assignee: SpineEX, Inc., Fremont, CA (US)

( * ) Notice: Subject to any disclaimer, the term of this patent is extended or adjusted under 35 U.S.C. 154(b) by 111 days.

(21) Appl. No.: 16/001,852

(22) Filed: Jun. 6, 2018

(65) Prior Publication Data

US 2018/0303626 A1 Oct. 25, 2018

Related U.S. Application Data

(63) Continuation of application No. 15/859,241, filed on Dec. 29, 2017, now Pat. No. 10,188,527, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4455* (2013.01); *A61F 2/4611* (2013.01); *A61F 2/4465* (2013.01);
(Continued)

(58) Field of Classification Search
CPC ...... A61F 2/447; A61F 2/4455; A61F 2/4465; A61F 2/46; A61F 2/4611;
(Continued)

(56) References Cited

U.S. PATENT DOCUMENTS 6,641,614 B1 * 11/2003 Wagner ............... A61F 2/4455
623/17.15
2002/0151977 A1 * 10/2002 Paes ...................... A61F 2/442
623/17.11
(Continued)

OTHER PUBLICATIONS

Japanese Patent Office, Office Action in Japanese Application No. 2016-537917, dated Jun. 4, 2018, 9 pages.

*Primary Examiner* — Amy R Sipp
(74) *Attorney, Agent, or Firm* — SpineEX, Inc.

(57) ABSTRACT

An expandable housing for an interbody fusion system has movable tapered external helical threaded members that travel along tracking to operably engage against the top and bottom shell members, urging them apart to cause expansion in the height of the housing. In an embodiment, the tapered members are disposed in a dual arrangement such that independent engagement of the tapered members along lateral portions of the top and bottom shells cause an angular tilt to the exterior surface of the housing when the tapered members are moved to different degrees. This function permits adjustment in the angular relationship between adjacent vertebrae and assists the lordotic adjustment of the patient's spine. When the functions of the device are used in combination by the surgeon, the device provides an effective tool for in situ adjustment when performing lateral lumbar interbody fusion.

21 Claims, 23 Drawing Sheets

Related U.S. Application Data continuation of application No. 14/473,200, filed on Aug. 29, 2014, now Pat. No. 9,889,019.

(60) Provisional application No. 61/871,780, filed on Aug. 29, 2013.

(52) U.S. Cl.
CPC ........... *A61F 2002/30462* (2013.01); *A61F 2002/30507* (2013.01); *A61F 2002/30523* (2013.01); *A61F 2002/30525* (2013.01); *A61F 2002/30538* (2013.01); *A61F 2002/30556* (2013.01); *A61F 2002/30566* (2013.01); *A61F 2002/4627* (2013.01)

(58) Field of Classification Search
CPC ...... A61F 2002/4475; A61F 2002/4625; A61F 2002/4627; A61F 2002/4638; A61B 17/8875; A61B 17/885
See application file for complete search history.

(56) References Cited

U.S. PATENT DOCUMENTS

2009/0210062 A1\* 8/2009 Thalgott ............... A61F 2/4465
623/17.16
2010/0323327 A1 12/2010 Eriksson et al.

\* cited by examiner

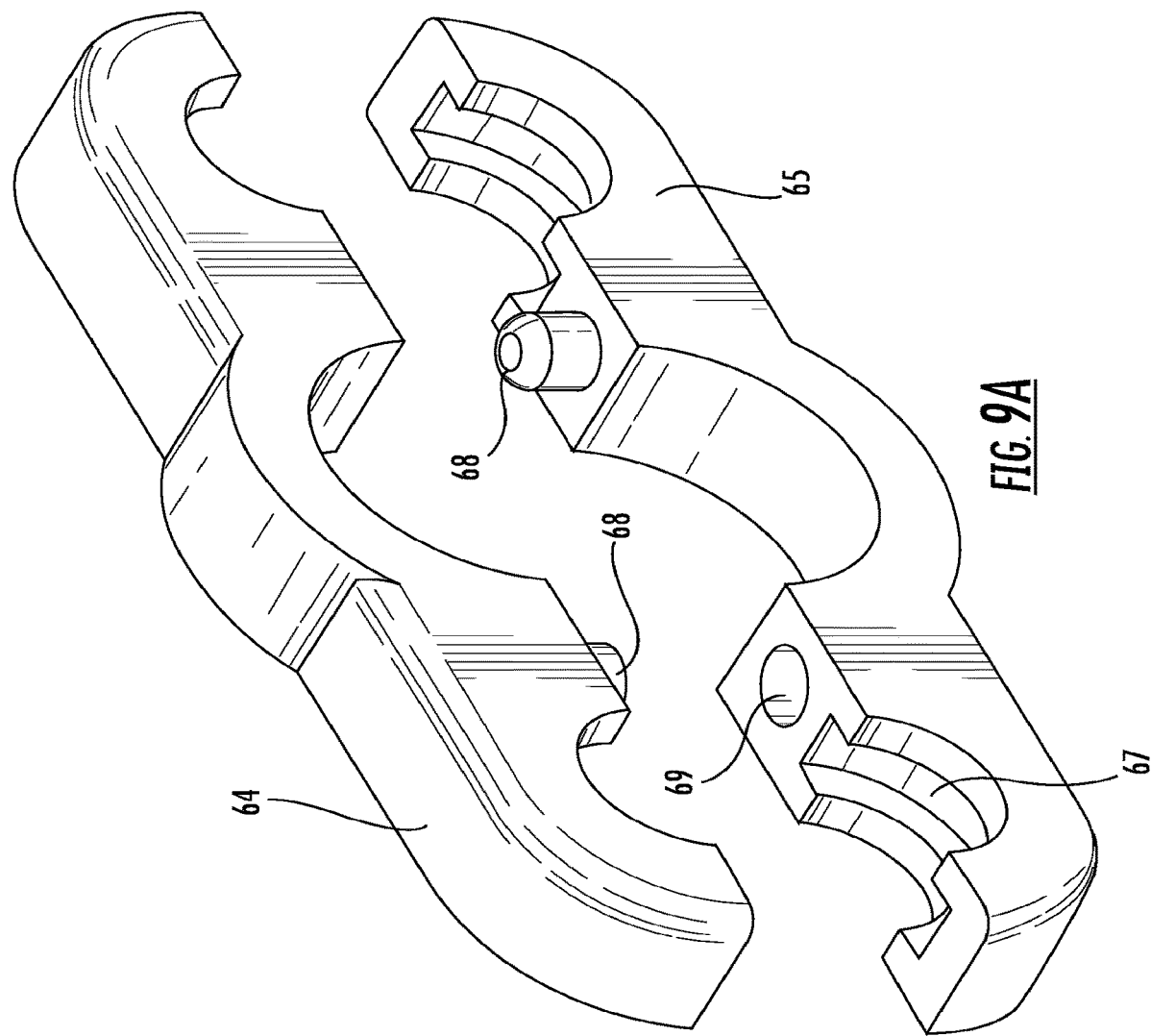

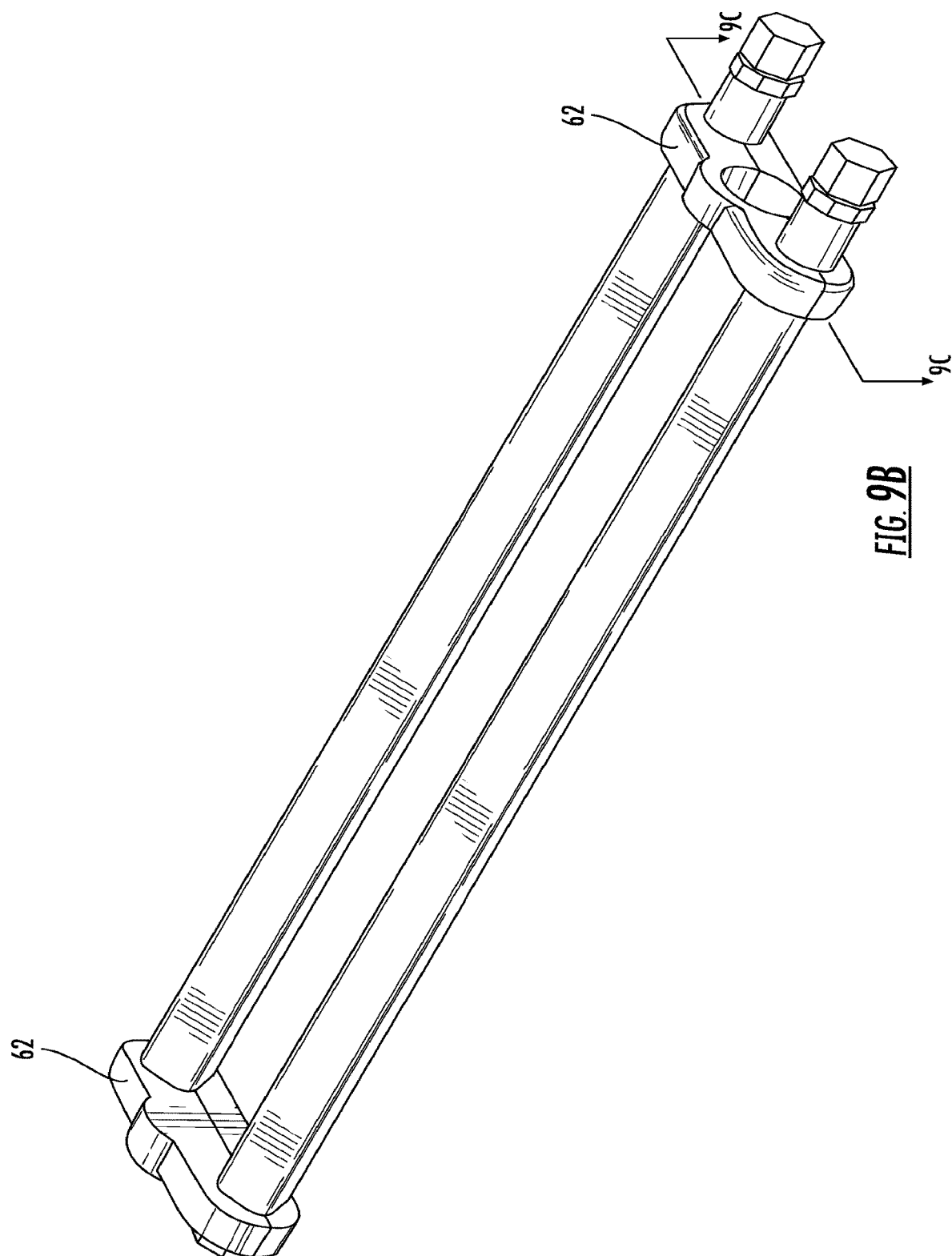

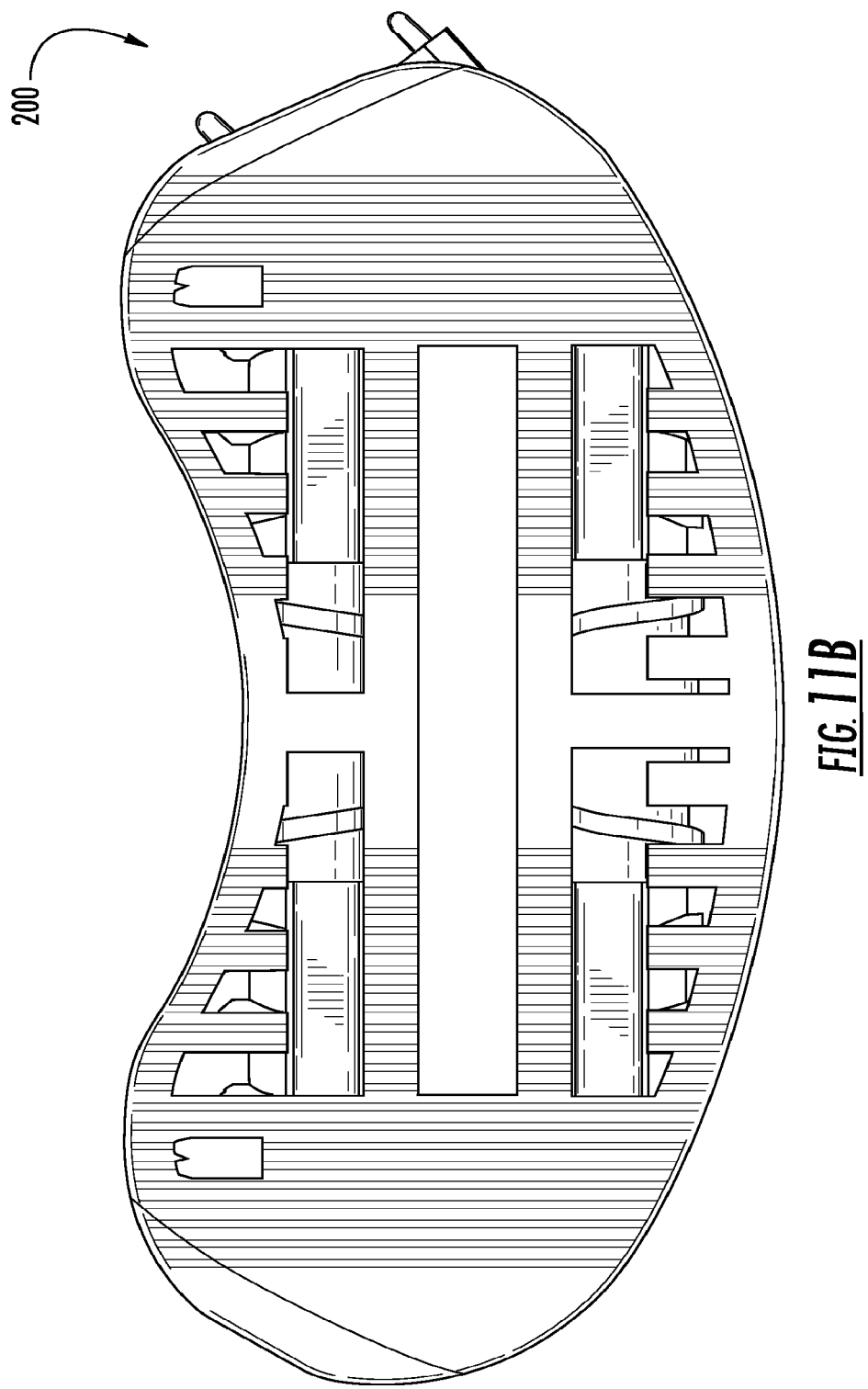

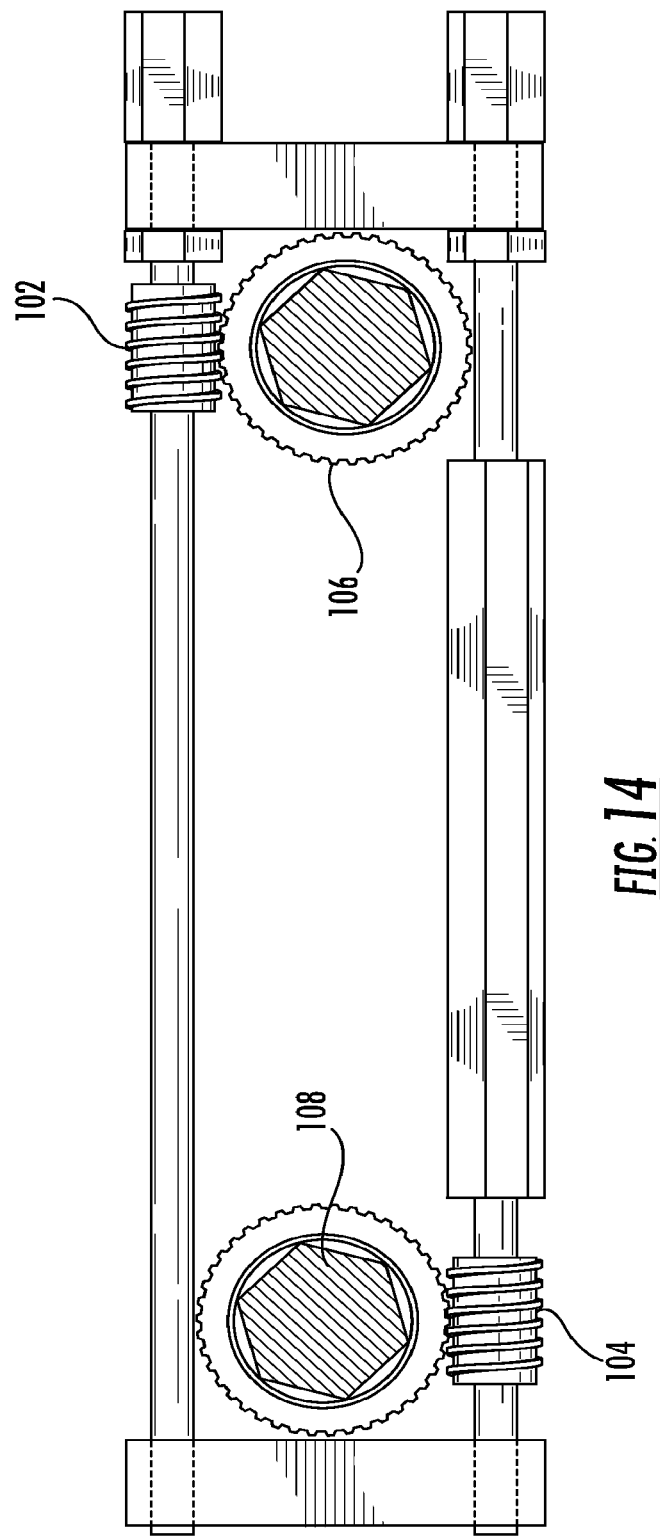

EXPANDABLE AND ADJUSTABLE LORDOSIS INTERBODY FUSION SYSTEM

RELATED APPLICATIONS

This application is a continuation of U.S. application Ser. No. 15/859,241 filed Dec. 29, 2017 entitled "EXPANDABLE AND ADJUSTABLE LORDOSIS INTERBODY FUSION SYSTEM," which is a continuation of U.S. application Ser. No. 14/473,200 filed Aug. 29, 2014 entitled "EXPANDABLE AND ADJUSTABLE LORDOSIS INTERBODY FUSION SYSTEM," which claims priority to U.S. provisional patent application No. 61/871,780 filed Aug. 29, 2013 entitled EXPANDABLE LATERAL INTERBODY FUSION SYSTEM, the disclosures of all of which are hereby incorporated by reference in their entirety.

TECHNICAL FIELD

The invention relates to surgical procedures and apparatus for treating lumbar back pain.

BACKGROUND

Lumbar spinal fusion is a surgical procedure to correct problems relating to the human spine. It generally involves removing damaged disc and bone from between two vertebrae and inserting bone graft material that promotes bone growth. As the bone grows, the two vertebrae join, or fuse, together. Fusing the bones together can help make that particular area of the back more stable and help reduce problems related to nerve irritation at the site of the fusion. Fusions can be done at one or more segments of the spine.

Interbody fusion is a common procedure to remove the nucleus pulposus and/or the annulus fibrosus that compose the intervertebral disc at the point of the back problem and replace it with a cage configured in shape and dimension to restore the distance between adjacent vertebrae to that of a proper condition. Surgical approaches to implement interbody fusion vary, and access to the patient's vertebral column can be made through the abdomen or back. One other surgical method for accomplishing lumbar spinal fusion in a less invasive way involves accessing the vertebral column through a small incision on the side of the body. This procedure is known as lateral lumbar interbody fusion.

Once the intervertebral disc is removed from the body during the lateral lumbar interbody fusion, the surgeon typically forces different trial implants between the vertebral endplates of the specific region to determine the appropriate size of the implant for maintaining a distance between the adjacent vertebrae. Another consideration is to maintain the natural angle between lumbar vertebral bodies to accommodate the lordosis, or natural curvature, of the spine. Therefore, during selection of a cage for implantation, both intervertebral disc height and lordosis must be considered. Prior art fusion cages are often pre-configured to have top and bottom surfaces angles to one another to accommodate the natural curvature of the spine. It is unlikely that these values can be determined precisely prior to the operation, which is a drawback in present procedures. Prepared bone graft is generally packed into the cage implant once it is properly sized and before it is inserted in between the vertebral bodies.

Present lateral interbody fusion cage devices are generally limited to providing height expansion functions, but not a lordotic adjustment capability. In implementing a trial-and-error approach to sizing and fitting the interbody fusion cage into the target region for the particular geometric configuration for that patient, the patient is subjected to significant invasive activity. The bone graft material is generally added and packed in to the fusion device after the desired height expansion has been reached and final adjustments made.

SUMMARY

An embodiment of the device comprises an expandable housing comprised of opposing shell members. Movable tapered screw-like elements having an external helical thread are disposed in the housing and operably engage against the top and bottom shell members, urging them apart to cause expansion in the height of the housing. This function permits adjustment of the distance (height) between adjacent vertebrae when in place. The tapered members are disposed in a dual arrangement such that independent engagement of the tapered members along lateral portions of the top and bottom shells cause an angular tilt to the exterior surface of the housing when the wedge members are moved to different degrees. This function permits adjustment in the angular relationship between adjacent vertebrae and assists the lordotic adjustment of the patient's spine. When the functions of the device are used in combination by the surgeon, the device provides an effective tool for in situ adjustment when performing lateral lumbar interbody fusion.

An embodiment of the device further comprises a track configuration within the housing for guiding the tapered external helical threaded members in their engagement with the top and bottom shell members. The track comprises raised elements on each of the interior surfaces of the top and bottom shell members that permit an interlocking engagement for lateral stability of the housing when in a contracted position. As the housing expands, the track area provides space for storage of bone graft material. One embodiment may provide for an elastic membrane to be positioned around the housing to prevent bone graft material from seeping out of the cage and to provide a compressive force around the cage to provide structural stability to the housing.

An embodiment of the device further comprises drive shafts for operating the tapered external helical threaded members. The drive shafts permit the surgeon, through the use of a supplemental tool, to manipulate the shafts which operatively move the tapered external helical threaded members in controlling the expansion of the housing and angular adjustment of the top and bottom shell members for in situ fitting of the interbody fusion device. A locking mechanism is provided for preventing rotation of the shafts when the tool is not engaged and after manipulation by the tool is completed. The tool also facilitates insertion of bone graft material into the fusion body during in situ adjustment.

An embodiment of the present invention provides a surgeon with the ability to both expand the fusion cage and adjust the lordotic angle of the fusion cage in situ during operation on a patient and to introduce bone graft material at the operation site while the device is in place. This embodiment of the present invention therefore provides a fusion cage having geometric variability to accommodate the spinal condition unique to each patient.

Embodiments of the present invention therefore provide an interbody cage device for use in lateral lumbar interbody fusion procedures that combines the functions of height expansion for adjusting the distance between adjacent vertebrae with lordotic adjustment to control the angular relationship between the vertebrae. Embodiments of the inventive interbody cage device further provide a storage capacity for containing bone graft material in the interbody cage device as disc height and lordotic adjustment takes place in situ.

The present invention also provides a device that may be used in environments other than in interbody fusion applications. It may generally be used to impart a separating effect between adjacent elements and to impart a variable angular relationship between the elements to which it is applied.

These and other features of the present invention are described in greater detail below in the section titled DETAILED DESCRIPTION OF THE INVENTION.

BRIEF DESCRIPTION OF THE DRAWINGS

An embodiment of the present invention is described herein with reference to the following drawing figures, with greater emphasis being placed on clarity rather than scale:

FIG. 9A is a perspective expanded view of thrust bearing for the drive shaft.

FIG. 9B is a perspective view of the drive shafts and thrust bearings.

FIG. 11B is a top plan view of yet another embodiment of the device.

FIG. 14 is a view taken along lines 14-14 in FIG. 11A.

DETAILED DESCRIPTION OF EMBODIMENTS

Figure 1:
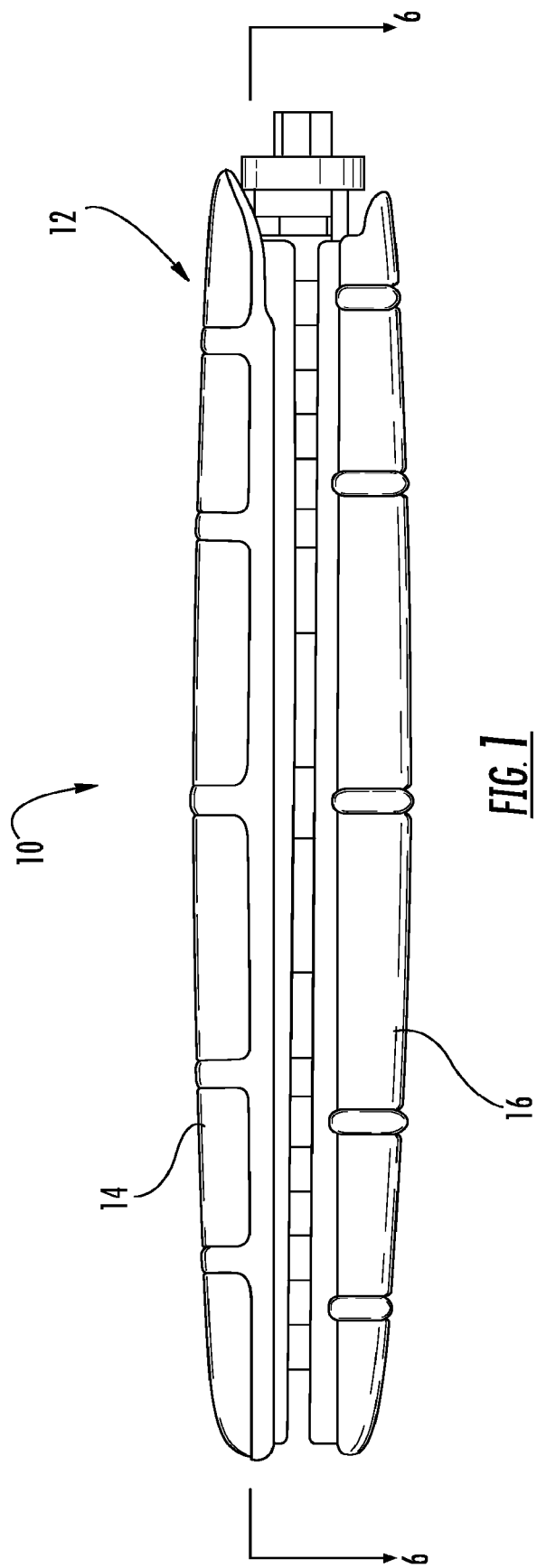
FIG. 1 is a view in side elevation from the side of the expandable shell device.
Figure 2:
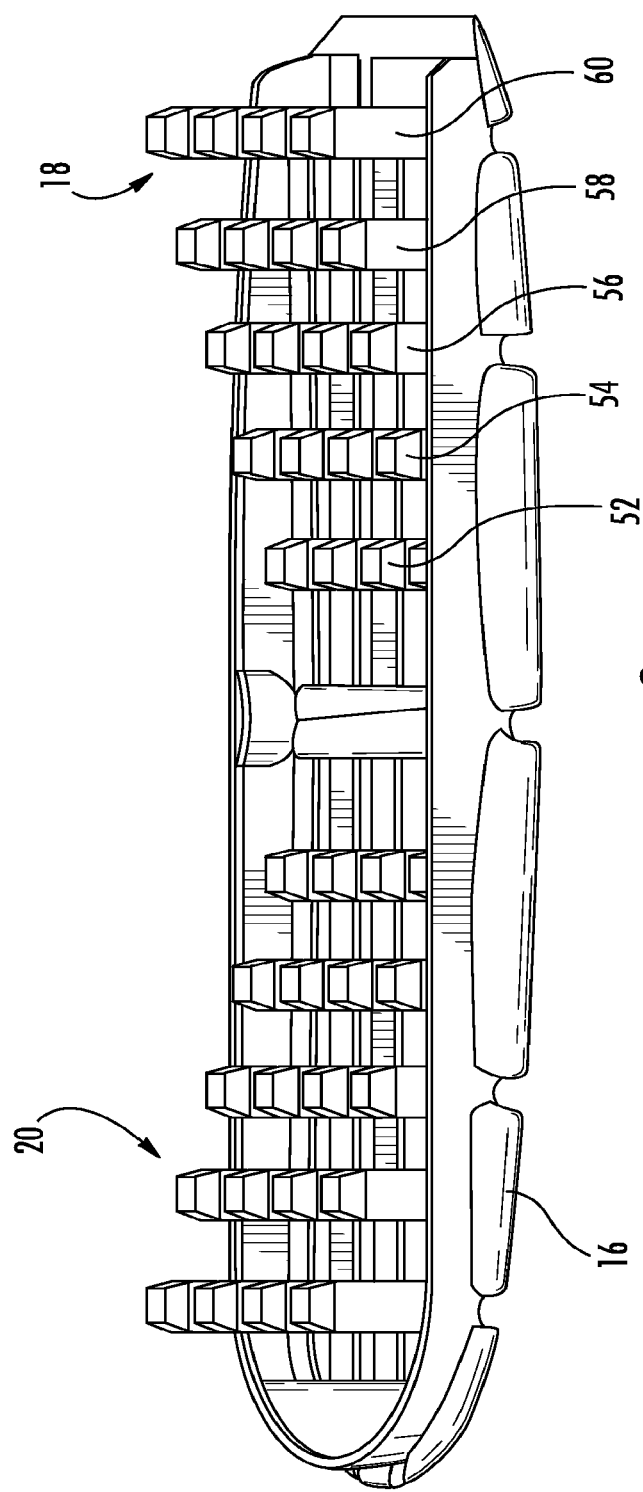
FIG. 2 is a perspective view of a bottom section of the expandable shell.
Figure 3:
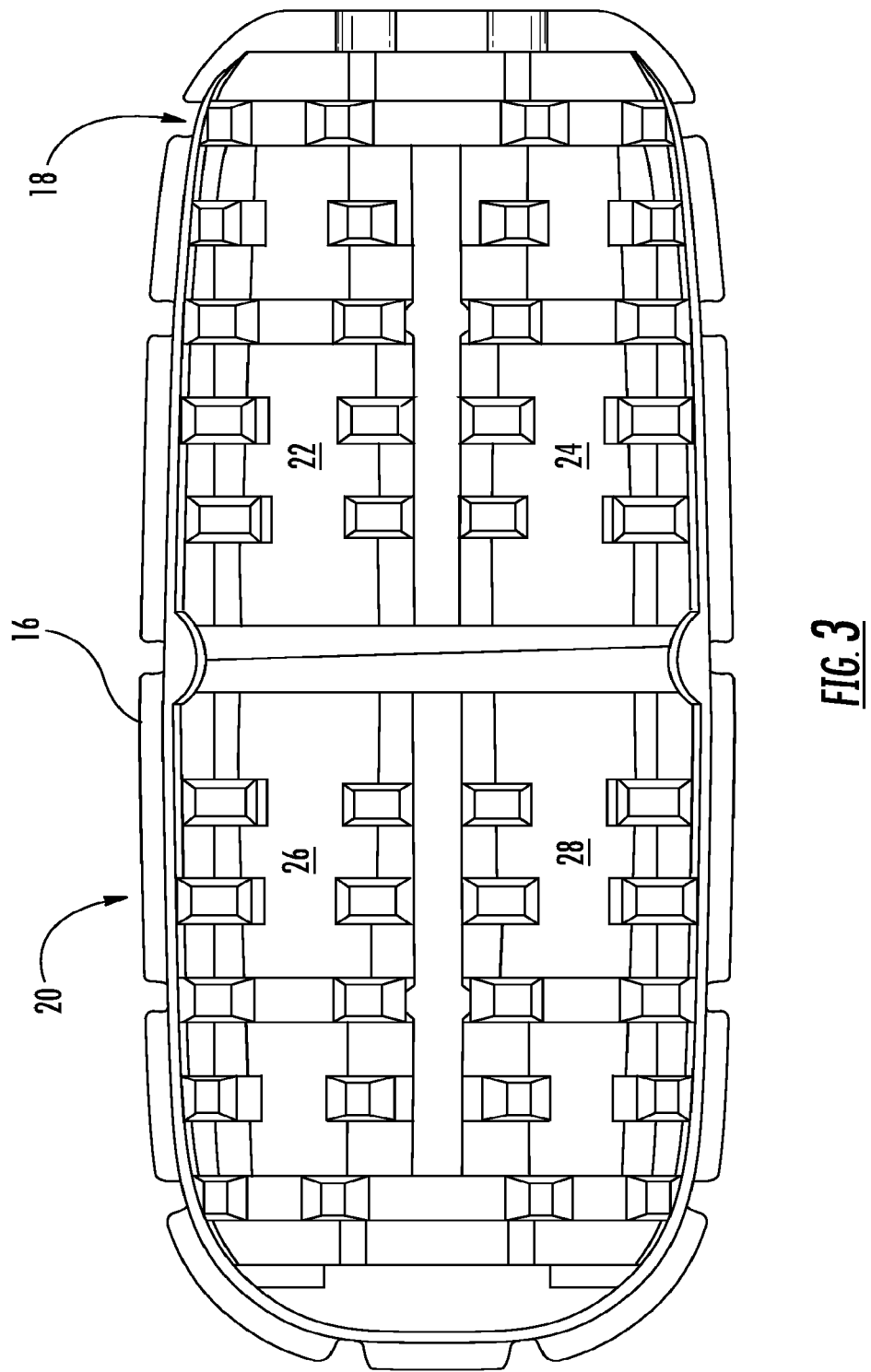
FIG. 3 is a top plan view of the bottom section of the expandable shell.
Figure 4:
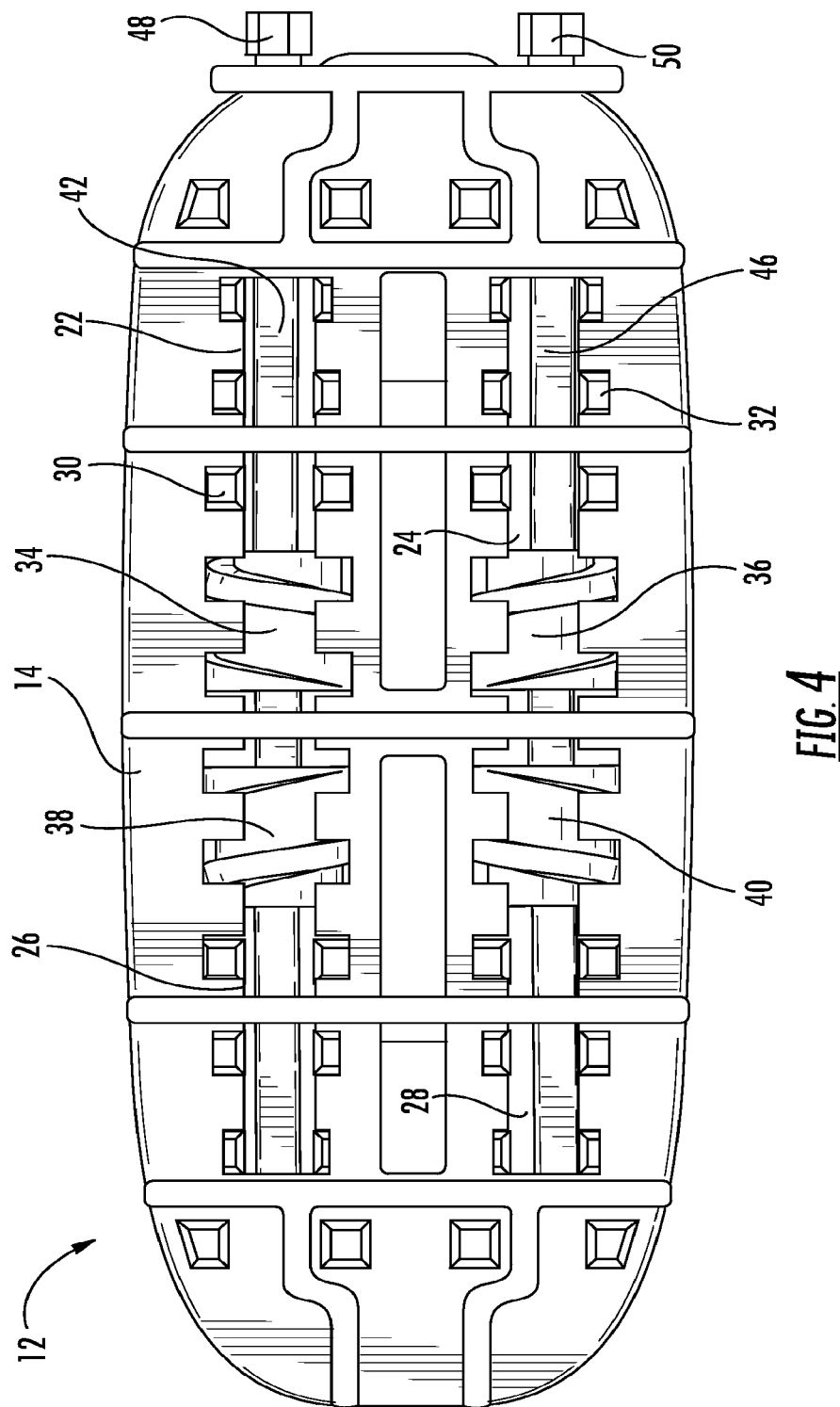
FIG. 4 is a top plan view of the expandable shell device.

With reference to the drawings figures, an interbody fusion body device is herein described, shown, and otherwise disclosed in accordance with various embodiments, including preferred embodiments, of the present invention. The interbody fusion device 10 is shown generally in FIG. 1. It is comprised of a housing 12 having a top shell 14 and a bottom shell 16. The overall housing may have a length of 50 mm and a width of 20 mm, as an example. The shell material may be comprised of a suitable material, such as titanium alloy (Ti-6AL-4V), cobalt chromium, or polyether ether ketone (PEEK). Other materials may be suitable that can provide sufficient compositional integrity and that have suitable biocompatible qualities. The interior of the shells are configured with a cascading step tracking 18 and 20 placed along their lateral edges. As shown in FIG. 2, step tracking 18 begins towards the midpoint of an inner surface of bottom shell 16 with successive track steps increasing in height as the tracking extends to a first end of bottom shell 16. Correspondingly, step-tracking 20 begins towards the midpoint of the inner surface of bottom shell 16 with successive track steps increasing in height as that portion of the tracking extends to a second opposite end of bottom shell 16. Step tracking 18 comprises dual track runs 22 and 24 while step tracking 20 comprises dual track runs 26 and 28 as shown in FIG. 3. Corresponding step tracking 30 and 32 is provided on top shell 14 as shown in FIG. 4. When the device is in its fully compressed state where top shell 14 lies adjacent to bottom shell 16, as shown in FIG. 1, step tracking 18 intermeshes with step tracking 30 and step tracking 20 intermeshes with step tracking 32.

Figure 5:
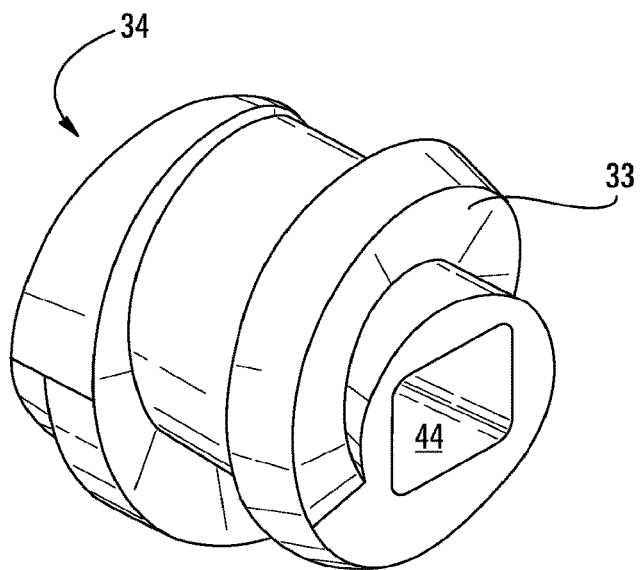
FIG. 5 is a perspective view of a tapered external helical threaded member.
Figure 5B:
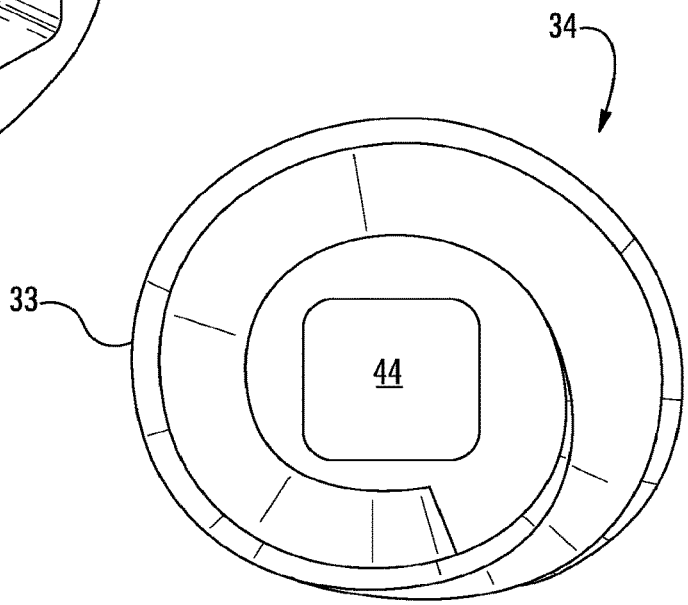
FIG. 5B is a view in side elevation from the front of the tapered external helical threaded member.
Figure 5A:
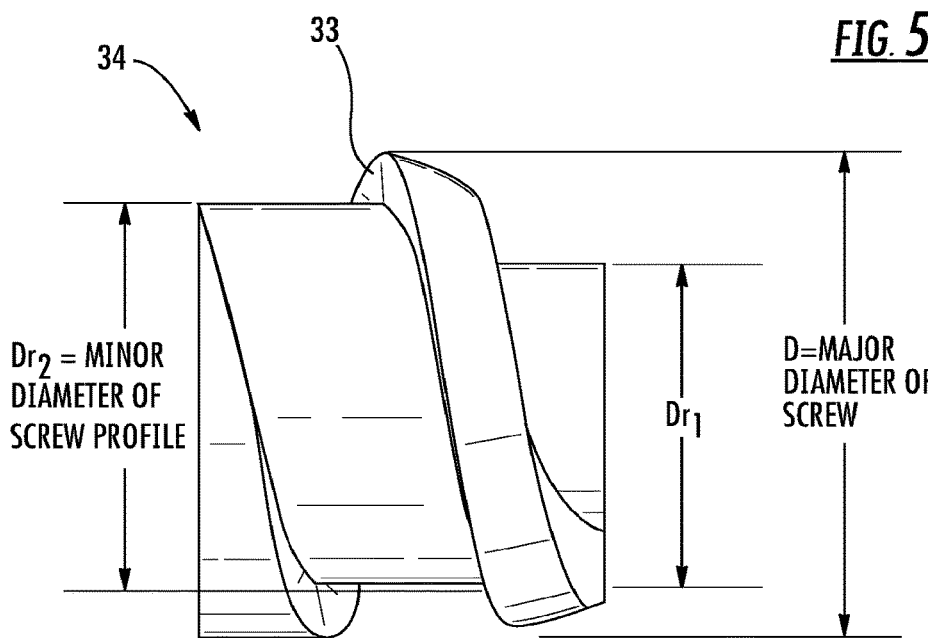
FIG. 5A is a view in side elevation from the side of the tapered external helical threaded member.

The respective track runs comprise a series of risers, or track steps, which are spaced apart to receive the threads of tapered external helical threaded members. The tapered external helical threaded members provide a wedging action for separating the top and bottom shell thereby increasing the height of the housing to effect expansion between the vertebral bodies in which the device is placed. As shown in FIG. 4, track run 22 receives tapered external helical threaded member 34, track run 24 receives tapered external helical threaded member 36, track run 26 receives tapered external helical threaded member 38, and track run 28 receives tapered external helical threaded member 40. Track run 22 aligns collinearly with track run 26 such that the travel of tapered external helical threaded members 34 and 38 within the respective track runs occurs within that collinear alignment. The thread orientation of tapered external helical threaded members 34 and 38 are opposite of each other such that their rotation will result in opposite directional movement with respect to each other. As shown in FIG. 4, a drive shaft 42 runs along the collinear span of track runs 22 and 26 and passes through tapered external helical threaded members 34 and 38. Shaft 42 has a square cross sectional configuration for engaging and turning the tapered external helical threaded members. As shown in FIG. 5, the central axial opening 44 of the tapered external helical threaded members are configured to receive and engage the shaft 42. Shaft 42 may alternatively comprise any shape for effectively creating a spline, such as a hexagonal shape, and central axial openings 44 may comprise a corresponding configuration for receiving that shape. As shaft 42 is rotated by its end 48 in a clockwise direction, tapered external helical threaded members 34 and 38 are rotated and their respective thread orientations cause the screws to travel apart from each other along track run 22 and track run 26, respectively. Correspondingly, as shaft 42 is rotated by its end 48 in a counter-clockwise direction, tapered external helical threaded members 34 and 38 are caused to travel towards each other along track run 22 and track run 26, respectively.

Similarly, track run 24 aligns collinearly with track run 28 such that the travel of tapered external helical threaded members 36 and 40 within the respective track runs occurs within that collinear alignment. The thread orientation of tapered external helical threaded members 36 and 40 are opposite of each other such that their rotation will result in opposite directional movement with respect to each other. Also, shaft 46 passes through and engages tapered external helical threaded members 36 and 40. However, the orientation of tapered external helical threaded members 36 and 40 is reversed from the orientation of tapered external helical threaded members 34 and 38. Under this orientation, as shaft 46 is rotated by its end 50 in a counter-clockwise direction, tapered external helical threaded members 36 and 40 are rotated and their respective thread orientations cause the screws to travel apart from each other along track run 24 and track run 28, respectively. Correspondingly, as shaft 46 is rotated by its end 50 in a clockwise direction, tapered external helical threaded members 36 and 40 are caused to travel towards each other along track run 24 and track run 28, respectively.

Figure 7A:
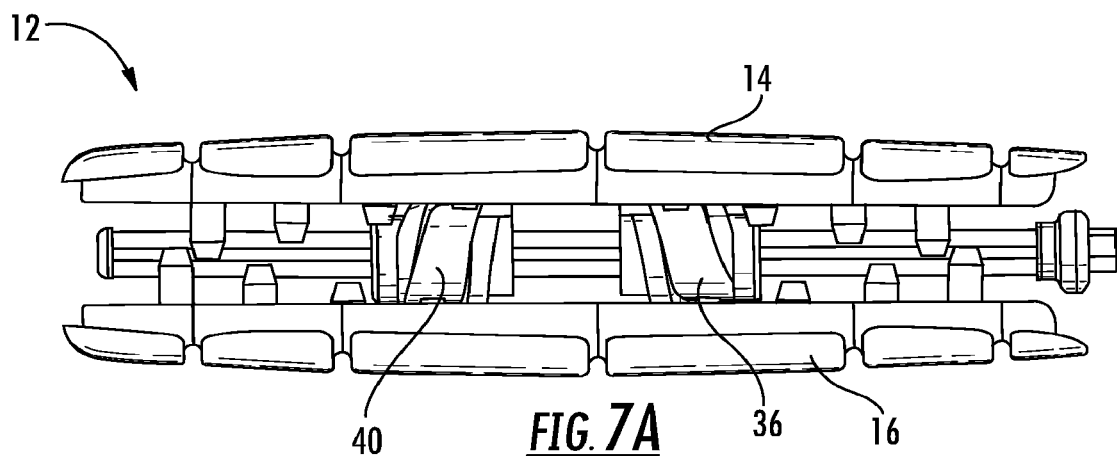
FIGS. 7A-7C are a series of views in side elevation of the device as it undergoes expansion.
Figure 7B:
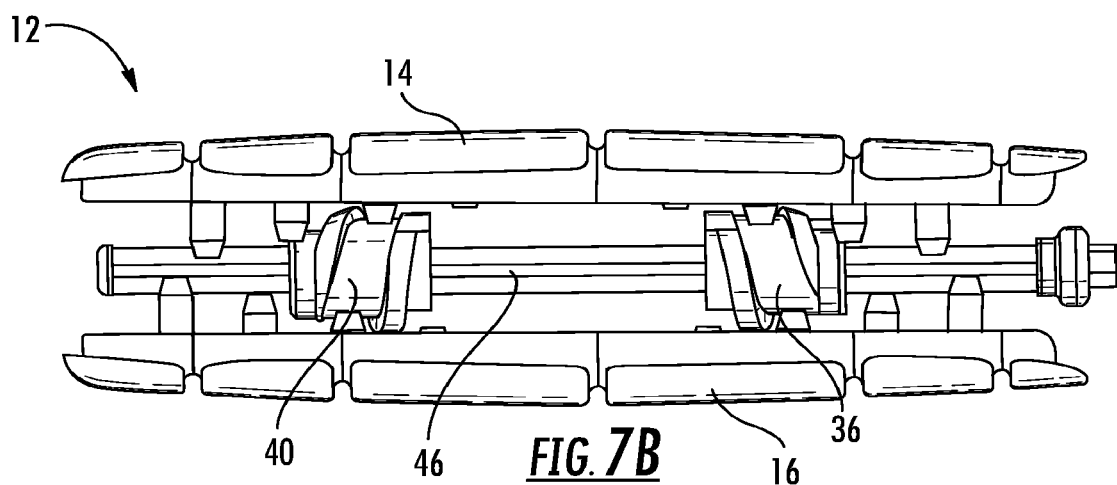
Figure 7C:
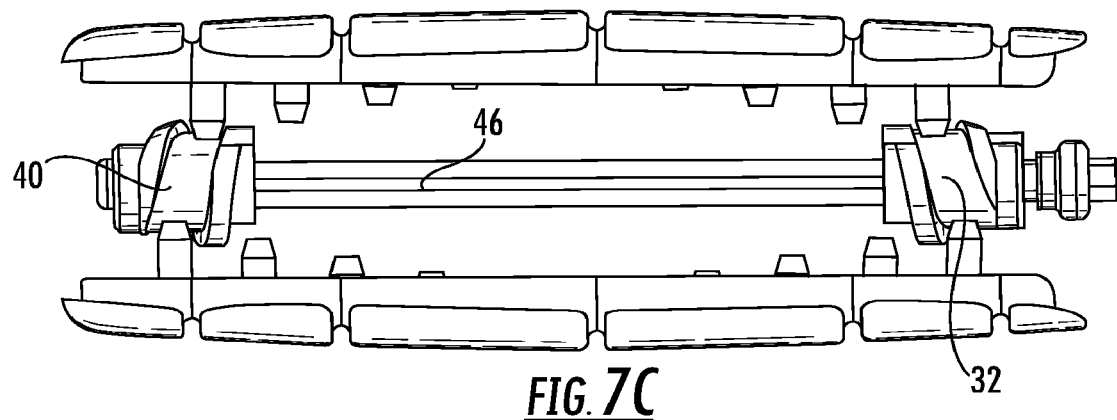
Figure 10:
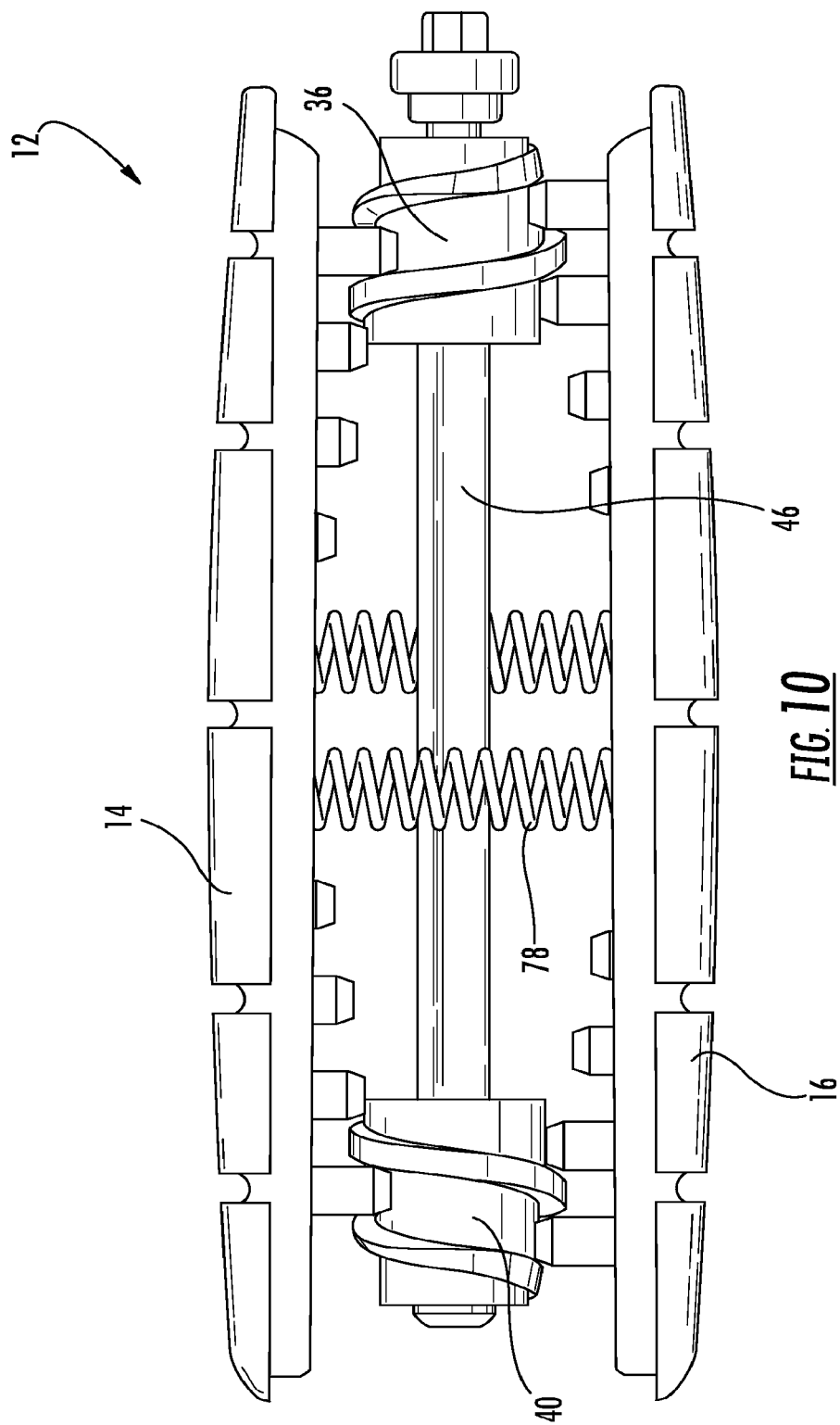
FIG. 10 is a side elevation view of the housing as expanded.

As shown in FIG. 2, the step tracking is configured with a cascading series of risers of increasing height. For example, each track run has risers 52-60 as shown for step tracking 18 in FIG. 2. As the thread of a tapered external helical threaded member travels into the gap between riser 52 and 54, the positional height of the tapered external helical threaded member body, as supported on risers 52 and 54, increases within the housing 12. As the tapered external helical threaded member continues to travel along the track run, its thread passes from the gap between risers 52 and 54 and enters the gap between risers 54 and 56 which raises the tapered external helical threaded member body further within housing 12 as it is supported on risers 54 and 56. As the tapered external helical threaded member continues its travel along the remainder of the step risers 58 and 60 its positional height increases further. As the positional height of the tapered external helical threaded member body increases, it urges top shell 14 apart from bottom shell 16 as shown in the series of FIGS. 7A-7C. The combined effect of rotating the tapered external helical threaded members to cause their movement towards the outer ends of the respective track runs causes an expansion of the housing 12 as shown in FIG. 7. The fully expanded shell is shown in FIG. 10. The housing 12 may be contracted by reversing the movement of the tapered external helical threaded members such that they travel back along their respective track runs towards the midpoint of the housing. The housing will optimally provide expansion and contraction to give the implant device a height over a range of around approximately 7.8 mm to 16.15 mm in the present embodiment. The device of this embodiment of the invention can be adapted to provide different expansion dimensions.

Figure 8:
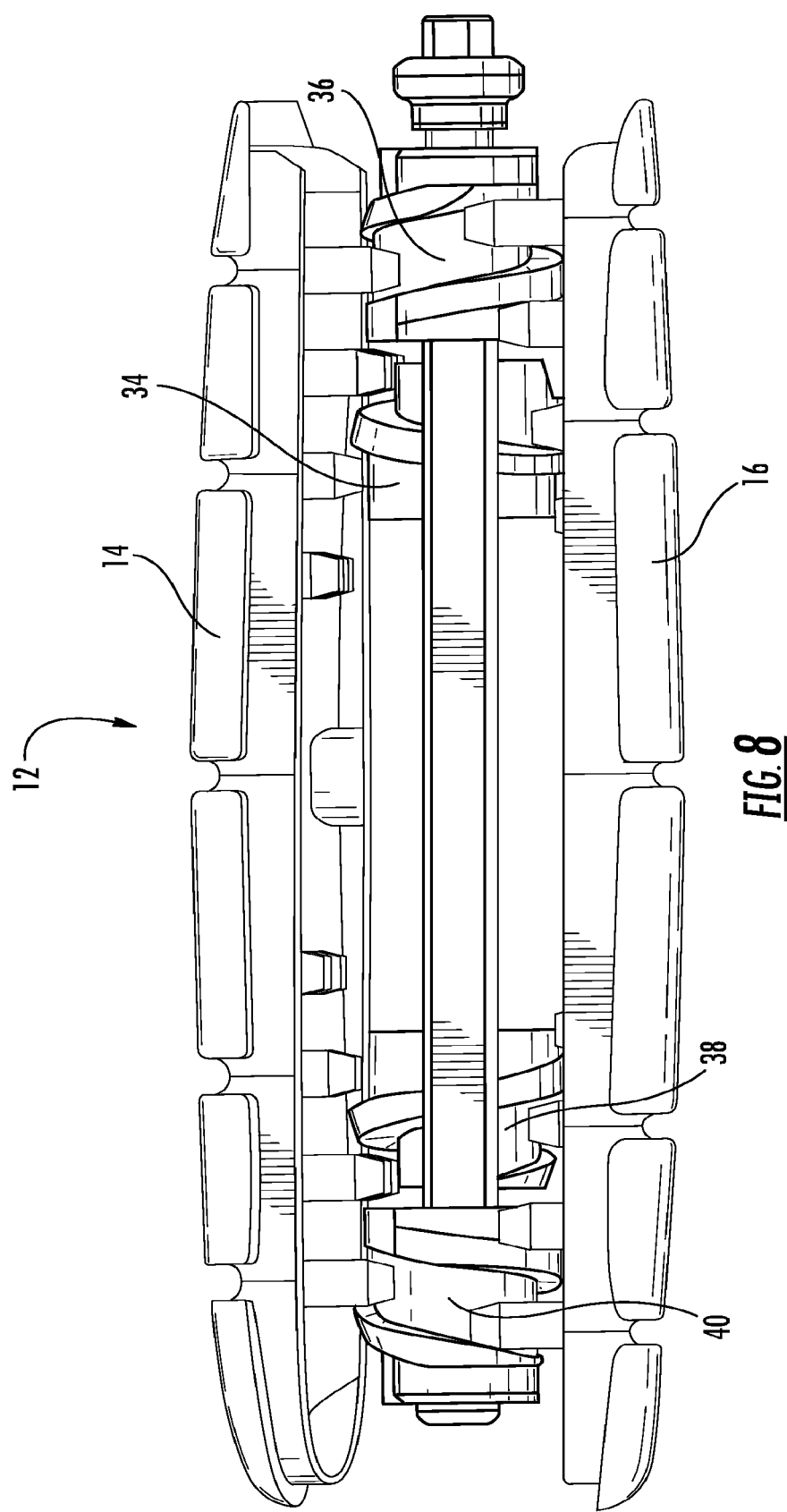
FIG. 8 is a view in side elevation of the device showing an expansion of the device to accommodate a lordotic effect.

The pairs of tapered external helical threaded members in each collinear dual track run may be rotated independently of the pair of tapered external helical threaded members in the parallel track run. In this arrangement, the degree of expansion of that portion of the housing over each collinear track run may be varied to adjust the lordotic effect of the device. As an example shown in FIG. 8, tapered external helical threaded members 36 and 40 have been extended to a particular distance along track run 24 and track run 28, respectively, causing the top shell 14 to separate from bottom shell 16 thereby expanding housing 12. Tapered external helical threaded members 34 and 38 have been extended to a lesser distance along parallel track run 22 and 26, respectively, causing that portion of the top shell over track runs 22 and 26 to separate from bottom shell to a lesser degree. The series of FIGS. 15A-15C show this effect where tapered external helical threaded members 36 and 40 are extended apart from each other in further increasing increments where the tapered external helical threaded members 34 and 38 maintain the same relative distance to each other.

Figure 15A:
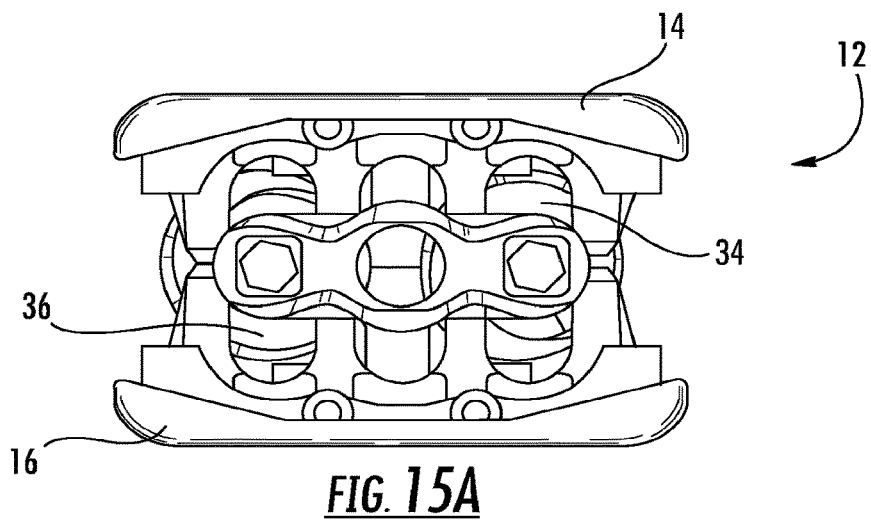
FIGS. 15A-C are a series of views in side elevation taken from the end of the device as it undergoes expansion showing the lordotic effect.
Figure 15B:
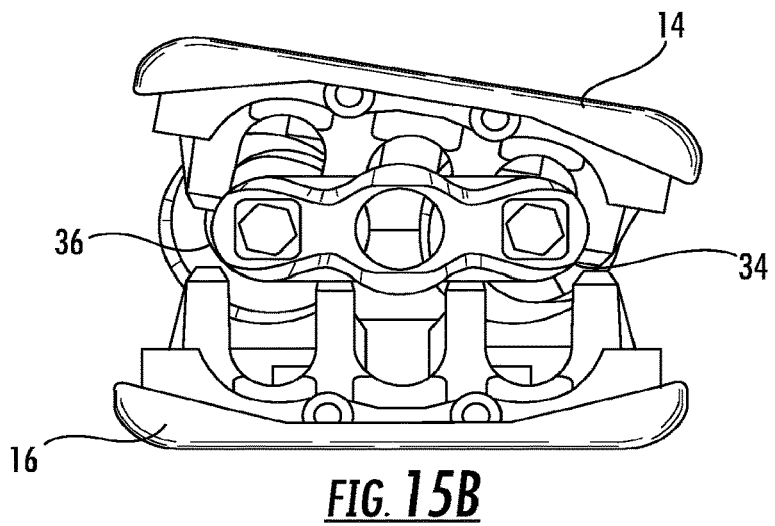
Figure 15C:
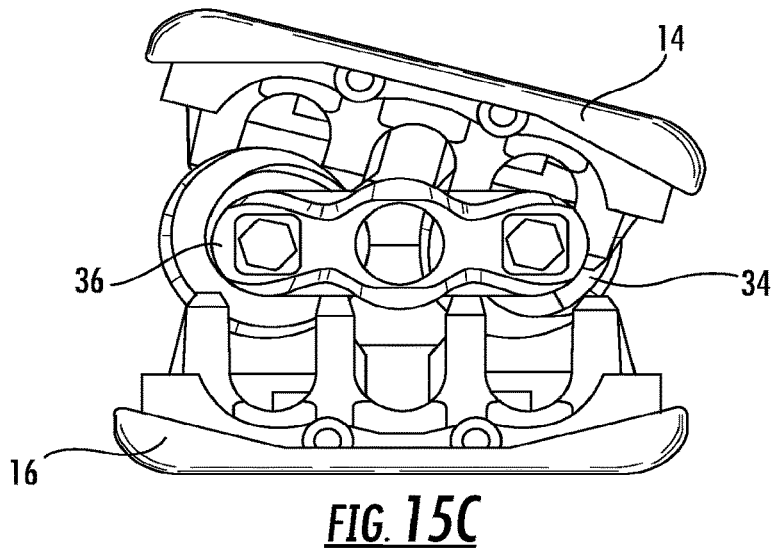

In FIG. 15A, the respective positioning of the set of tapered external helical threaded members 36-40 is approximately the same as the set of tapered external helical threaded members 34-38 in their respective tracking. In this position, the top shell 14 is essentially parallel with bottom shell 16. In FIG. 15B, the set of tapered external helical threaded members 36-40 move further distally apart along their tracking as the set of tapered external helical threaded members 34-38 remains at their same position in FIG. 15A. In this setting, the lateral edge of top shell 14 along which tapered external helical threaded members 36 and 40 travel is moved higher with respect to the lateral edge of top shell 14 along which tapered external helical threaded members 34 and 38 travel, giving a tilt to top shell 14 with respect to bottom shell 16. In FIG. 15C, the set of tapered external helical threaded members 36-40 move even further distally apart along their tracking with respect to that of the set of tapered external helical threaded members 34-38, giving an even greater tilt to top shell 14 with respect to bottom shell 16. Through the independent movement of the respective tapered external helical threaded member sets, the device can achieve a lordotic effect of between 0° and 35° in the present embodiment. The device of this embodiment of the invention can be adapted to provide different lordotic tilt dimensions.

The tapered external helical threaded members have a configuration comprising a body profile that has an increasing minor diameter from $D_{r1}$ to $D_{r2}$ as shown in FIG. 5. The threads 33 have a pitch to match the spacing between the riser elements 52-60 in the tracking runs as shown in FIG. 4. Threads 33 can have a square profile to match the configuration between the risers, but other thread shapes can be used as appropriate. The increasing diameter and tapering aspect of the helical threaded members cause top shell 14 and bottom shell 16 to move apart as described above. The contact at the tops of the risers 52-60 is made at the minor diameter of the helical threaded member.

Figure 9C:
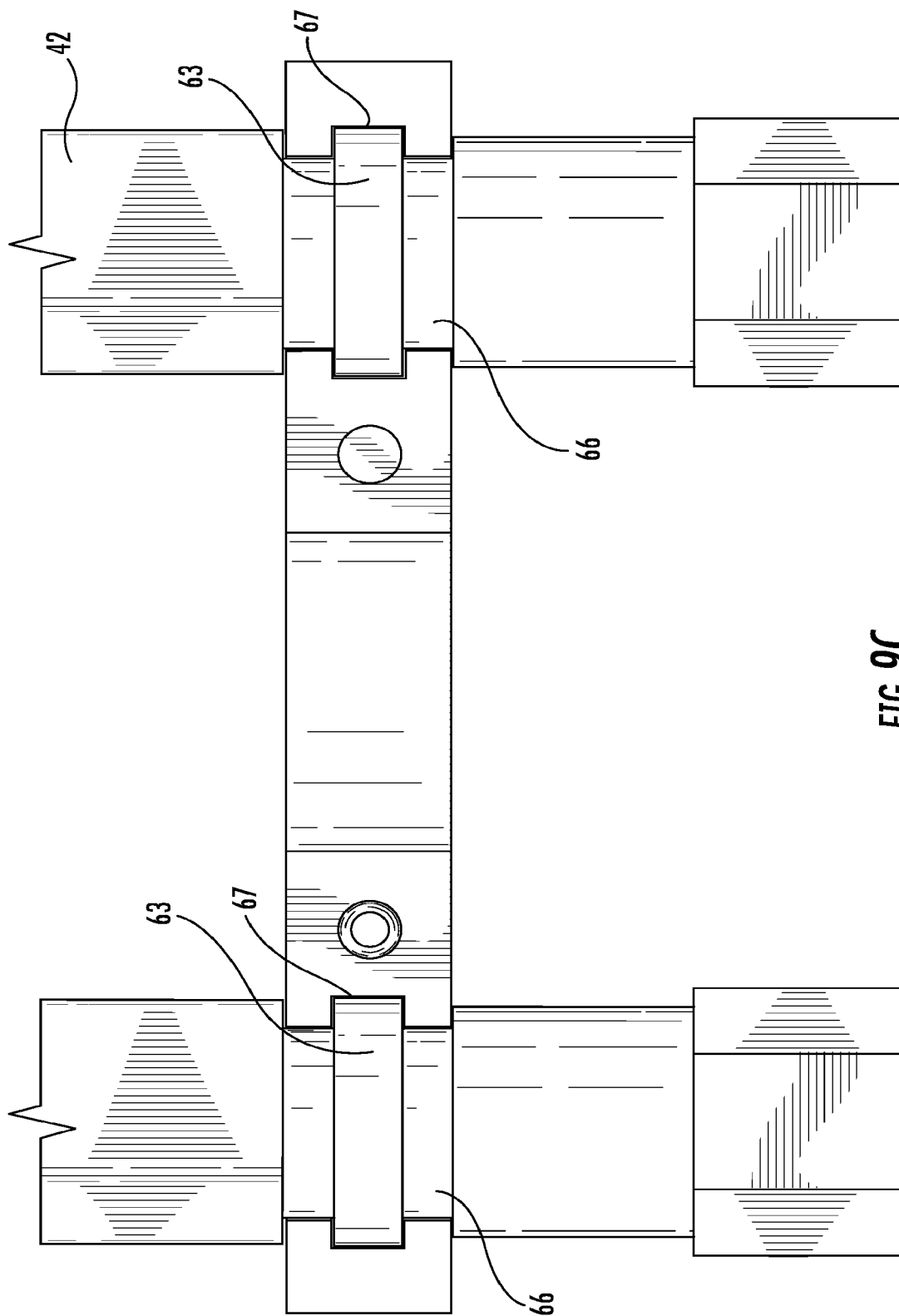
FIG. 9C is a top plan view in cross section of the area of engagement of the drive shafts with the thrust bearings.

Thrust bearings are provided to limit the axial direction motion of the drive shafts within shell 12. As shown in FIG. 9A, thrust bearing 62 comprises a two-piece yoke configuration that mate together and press-fit around ends of the shafts. The top part 64 of the thrust bearing yoke defines openings for receiving a round portion 66 of the shaft ends. In FIG. 9C, square shaft 42 has a rounded portion 66 of lesser diameter than the square portion of the shaft. A mating piece 65 of the thrust bearing engages with top part 64 to encircle the rounded portion 66 of drive shaft 42. Pin elements 68 in the top portion 64 and bottom portion 65 engages corresponding holes 69 in the mating piece to provide a press fit of the thrust bearing around the shaft.

Figure 6:
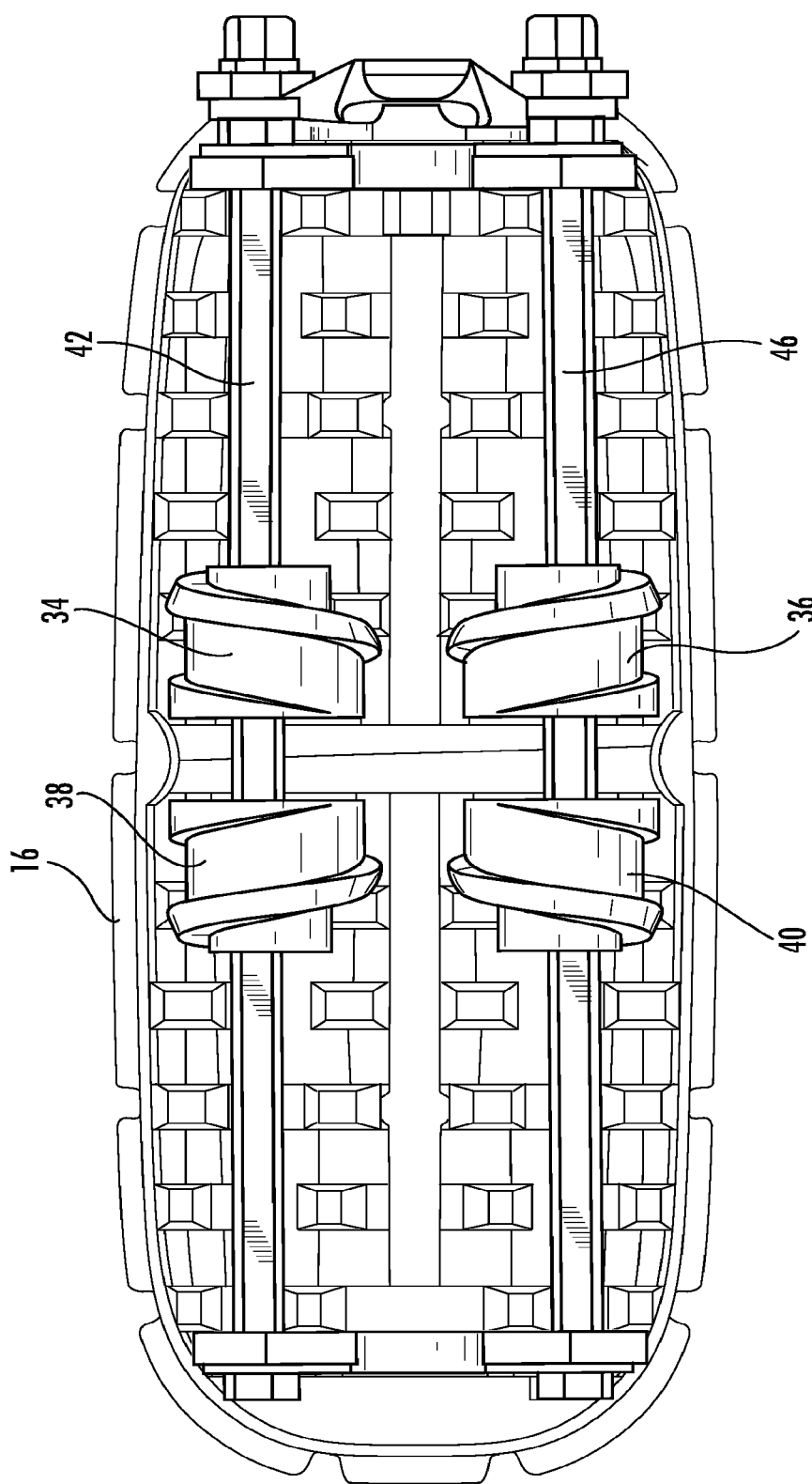
FIG. 6 is a cross-sectional view of the device taken along lines 6-6 in FIG. 1.

Journal grooves 67 can also be provided in thrust bearing 62. Shaft 42 can have an annular ridge 63 around its rounded portion 66 which is received in journal groove 67 as shown in FIG. 9C. A thrust bearing is provided at each end of the drive shafts as shown in FIG. 9B. As shown in FIG. 6, the thrust bearings restrict the axial movement of the drive shafts in the housing.

Figure 12A:
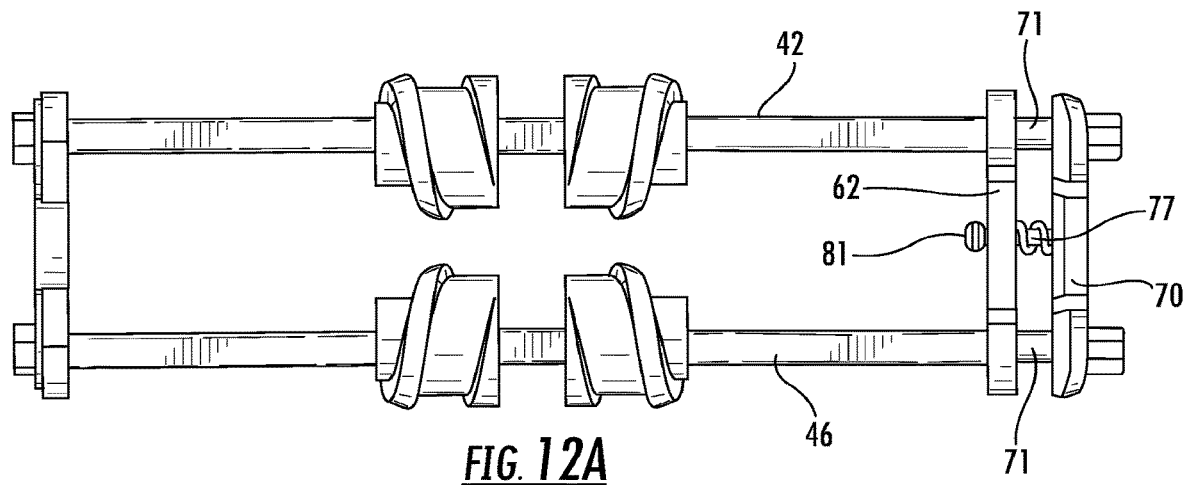
FIG. 12A is a top plan view of the drive shafts disengaged by the locking mechanism.
Figure 12B:
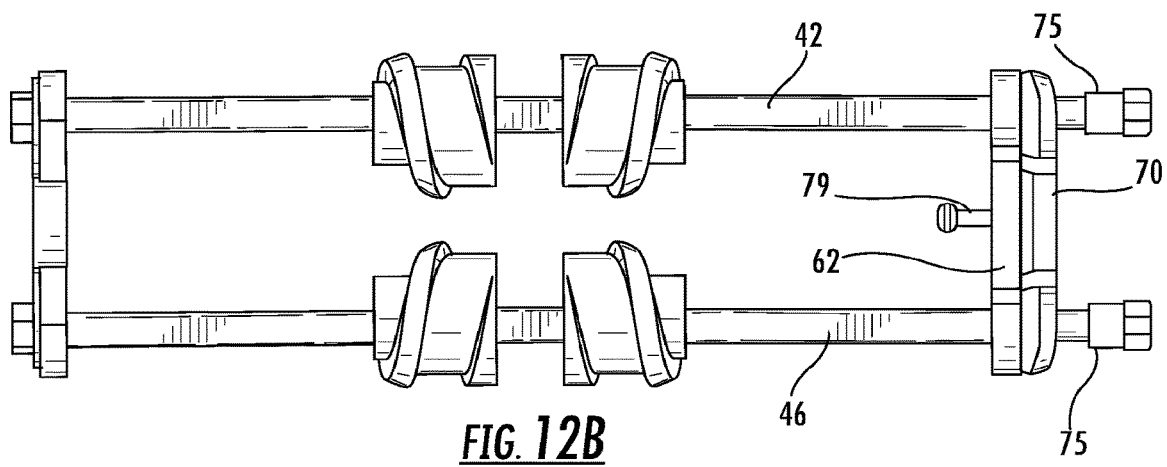
FIG. 12B is a top plan view of the drive shafts engaged by the locking mechanism.
Figure 13A:
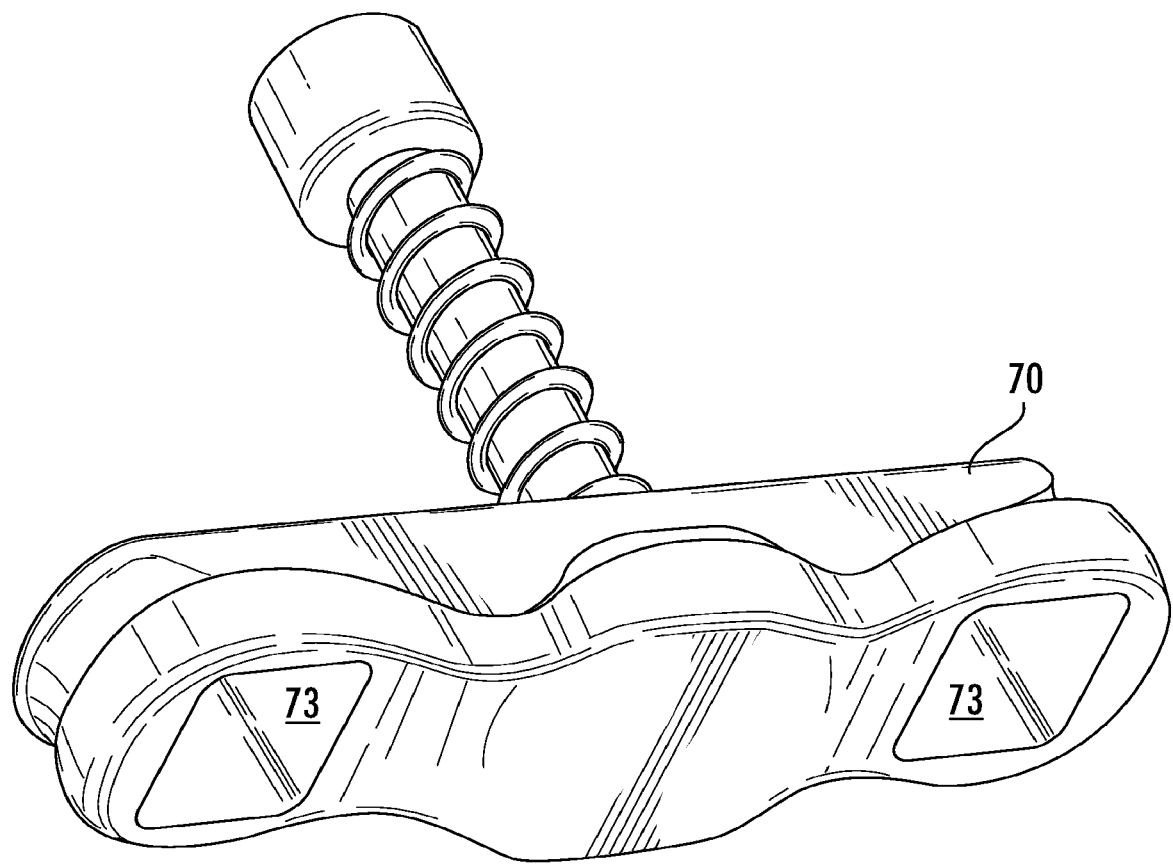
FIG. 13A is a perspective view of the locking mechanism.
Figure 13B:
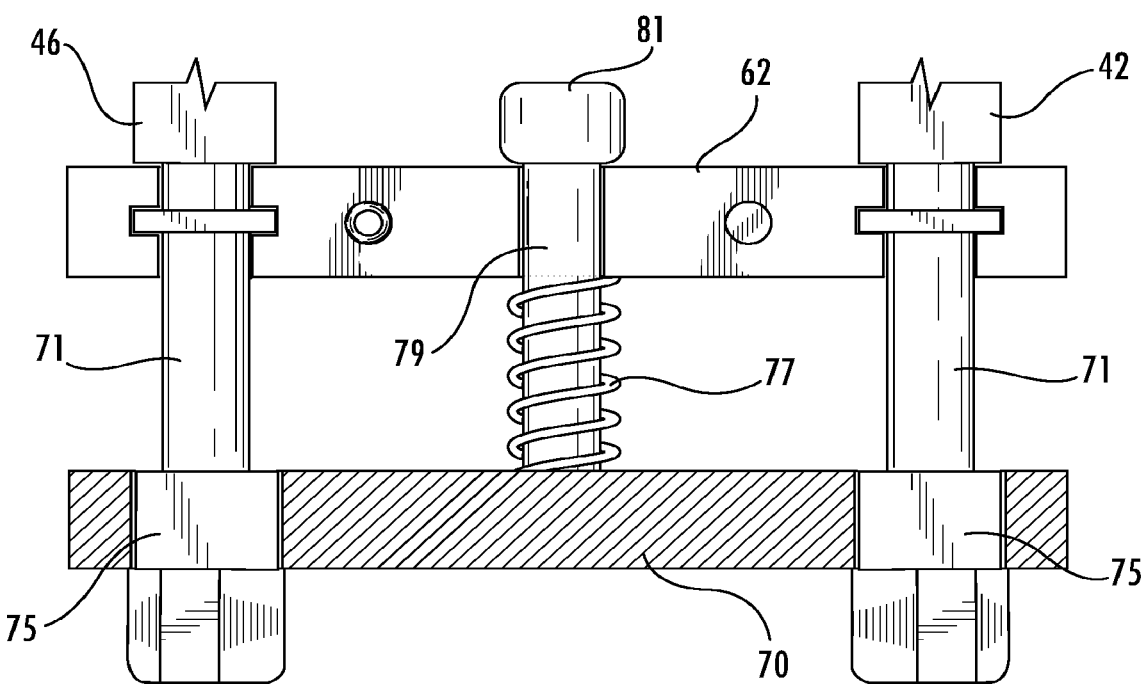
FIG. 13B is a top plan cross sectional view of the drive shafts disengaged by the locking mechanism.
Figure 13C:
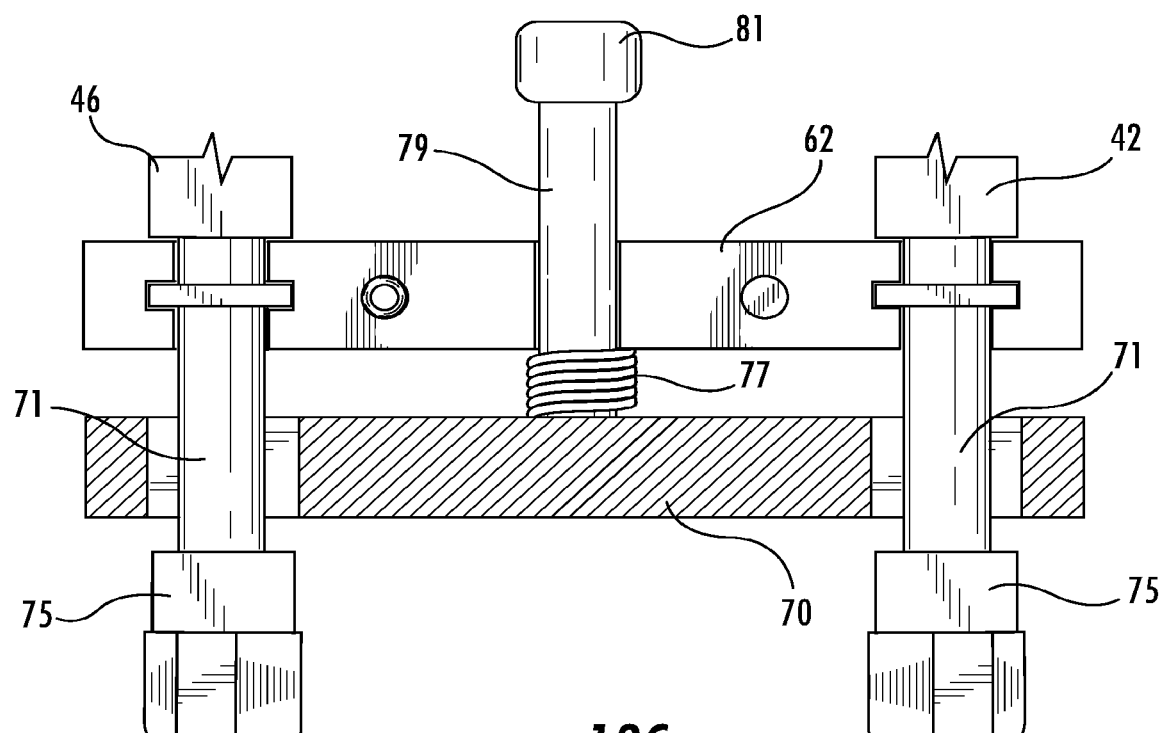
FIG. 13C is a top plan cross sectional view of the drive shafts engaged by the locking mechanism.

A safety lock is provided at the proximal end of the device for preventing unintended rotation of the shafts. As shown in FIGS. 12A and 12B, safety lock member 70 is provided for engagement with the proximal ends of drive shafts 42 and 46. The openings 73 in safety lock member 70 are configured with the shape of the cross-sectional configuration of the drive shafts (see FIG. 13A). A portion of the drive shafts has a narrowed, rounded configuration 71 such that the drive shaft can rotate freely while the rounded portion of the shaft is in alignment with the safety lock member openings 73 (see FIG. 13C). FIG. 12B shows this relationship among the safety lock member 70, thrust bearing 62 and drive shafts 42 and 46. When the non-narrowed portions 75 of the shafts are placed in alignment with the safety lock member openings 73, then rotation of the shafts is prevented (see FIG. 13B). FIG. 12A shows this relationship among the safety lock member 70, thrust bearing 62 and drive shafts 42 and 46. A compression spring 77 can be placed between thrust bearing 62 and safety lock member 70 to urge safety lock member back over the square portion 75 of the drive shafts. FIG. 12B shows a lock disengagement when the safety lock member 70 is pushed forward out of alignment with the square portions 75 and placed in alignment with the rounded portions 71 of shafts 42 and 46. Post 79 can be disposed between safety lock member 70 and thrust bearing 62 on which compression spring 77 can be positioned. Post 79 can be fixedly connected to safety lock member 70 and an opening can be provided in thrust bearing 62 through which post 79 can slide. Post 79 is provided with head 81 to limit the backward movement of safety lock member 70 from the compressive force of spring 77.

The interaction of the tapered external helical threaded members with the step tracking contributes to self-locking under a power screw theory. In considering the variables for promoting a self-locking aspect of the tapered threaded members, certain factors are relevant. In particular, those factors include the coefficient of friction of the materials used, such as Ti-6Al-4V grade 5, the length of pitch of the helical threads and the mean diameter of the tapered member. The following equation explains the relationship among these factors in determining whether the tapered external helical threaded members can self-lock as it travels along the step tracking:

$$T_R = \frac{F d_m}{2} \left( \frac{l + \pi f d_m \sec\alpha}{\pi d_m - f l \sec\alpha} \right)$$

The above equation determines the torque necessary to apply to the drive shafts engaging the tapered external helical threaded members for expanding the shell members. This torque is dependent upon the mean diameter of the tapered external helical threaded members, the load (F) applied by the adjacent vertebral bodies, the coefficient of friction (f) of the working material, and the lead (l) or, in this embodiment, the pitch of the helical threading. All of these factors determine the required operating torque to transform rotational motion into a linear lift to separate the shell members in accomplishing expansion and lordosis.

The following equation describes the relationship among the factors relating to the torque required to reverse the tapered external helical threaded members back down the tracking:

$$T_R = \frac{F d_m}{2} \left( \frac{\pi f d_m - l}{\pi d_m + f l} \right)$$

Under this equation, the torque required to lower the tapered external helical threaded members ($T_L$) must be a positive value. When the value of ($T_L$) is zero or positive, self-locking of the tapered external helical threaded members within the step tracking is achieved. If the value of ($T_L$) falls to a negative value, the tapered external helical threaded members are no longer self-locking within the step tracking. The factors that can contribute to a failure to self-lock include the compressive load from the vertebral bodies, the pitch and mean diameter of the helical thread not being adequately great, and an insufficient coefficient of friction of the material. The condition for self-locking is shown below:

$$\pi f d_m > l$$

Under this condition, it is necessary to select an appropriate combination of sufficient mean diameter size of the tapered member, along with the product material being a greater multiple than the lead or pitch in this particular application so that the tapered members can be self-locking within the step tracking. Based upon average values with a patient lying on their side, the lumbar vertebral body cross sectional area is around 2239 mm² and the axial compressive force at that area is 86.35 N. With the working material selected to be Ti-6Al-4V, the operating torque to expand shell housing 12 between L4-L5 of the vertebral column is around 1.312 lb-in (0.148 N-m), and the operating torque to contract shell housing 12 between L4-L5 of the vertebral column is around 0.264 lb-in (0.029 N-m).

Figure 11A:
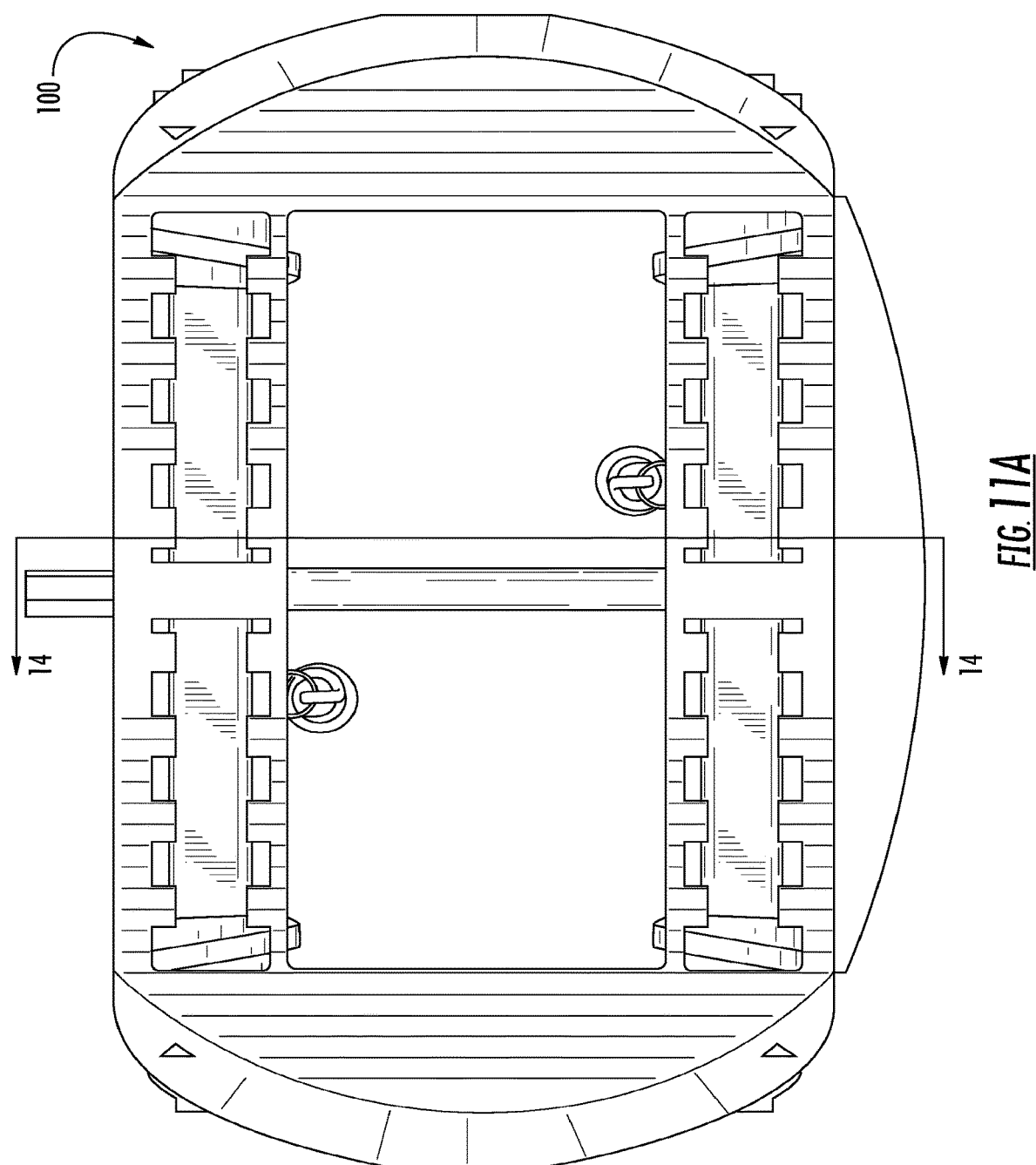
FIG. 11A is a top plan view of another embodiment of the device.

Alternate embodiments of the expandable shell housing provide for different surgical approaches. FIG. 11A shows housing 100 for use where a surgeon approaches the lumbar area from an anterior aspect of the patient. The general configuration of the tracking runs for this embodiment is similar to that for device 10, but the drive shafts for moving the tapered external helical threaded members are applied with a torque delivered from a perpendicular approach. For this, a dual set of worm gears 102 and 104 respectively transfer torque to drive shafts 106 and 108 as shown in FIG. 14.

FIG. 11B shows housing 200 for use where a surgeon approaches the lumbar area from a transforaminal aspect of the patient. The general configuration of the tracking runs for this embodiment is also similar to that for device 10, but the torque is applied to the drive shafts from an offset approach. For this, a dual set of bevel gears (not shown) may be used to transfer torque to drive shafts 206 and 208.

Housing 12 is provided with numerous niches and open areas in its surface and interior regions to accommodate the storage of bone grafting material. The interstitial spaces between the risers of the cascading step tracking also offers areas for receiving bone-grafting material. A membrane can be provided as a supplement around housing 12 to help maintain compression on the top and bottom shells and to hold in bone grafting material. Tension spring elements 78 can be provided to hold together top member 14 and bottom member 16 as shown in FIG. 10. These elements may also serve to provide an initial tension force in the direction opposite of the expansion against the interbody fusion device. This allows the tapered external helical threaded members to climb the risers in the event that contact between the outer shells and the vertebral bodies is not yet made.

Accordingly, this embodiment of the interbody fusion device of the instant invention is capable of expansion to provide support between vertebral bodies and accommodate the load placed on that region. Furthermore, the inventive interbody fusion device is capable of achieving a configuration that can provide an appropriate lordotic tilt to the affected region. The device, therefore, provides a significant improvement with regards to patient-specific disc height adjustment.

Figure 16:
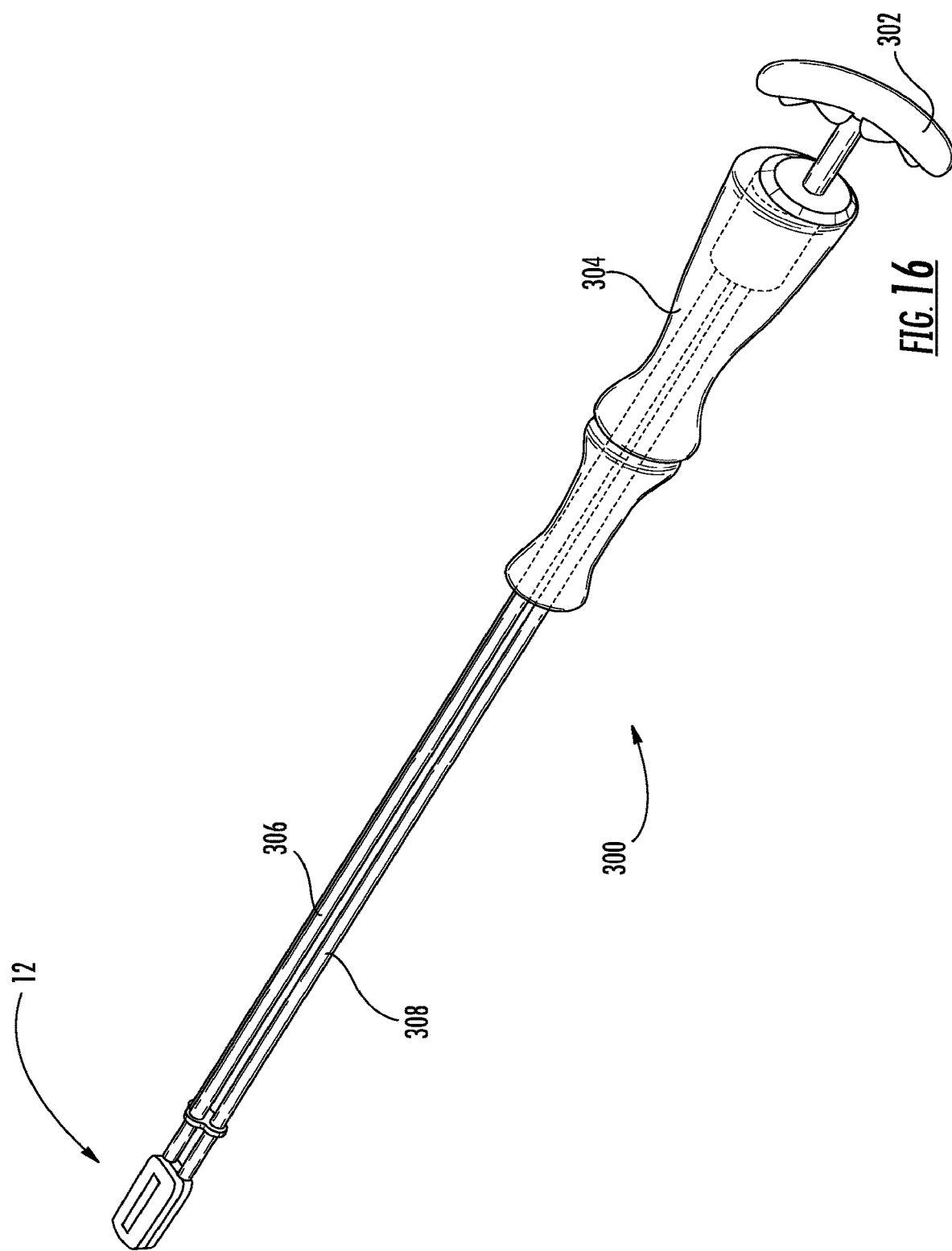
FIG. 16 is a perspective view of the operating tool.
Figure 17:
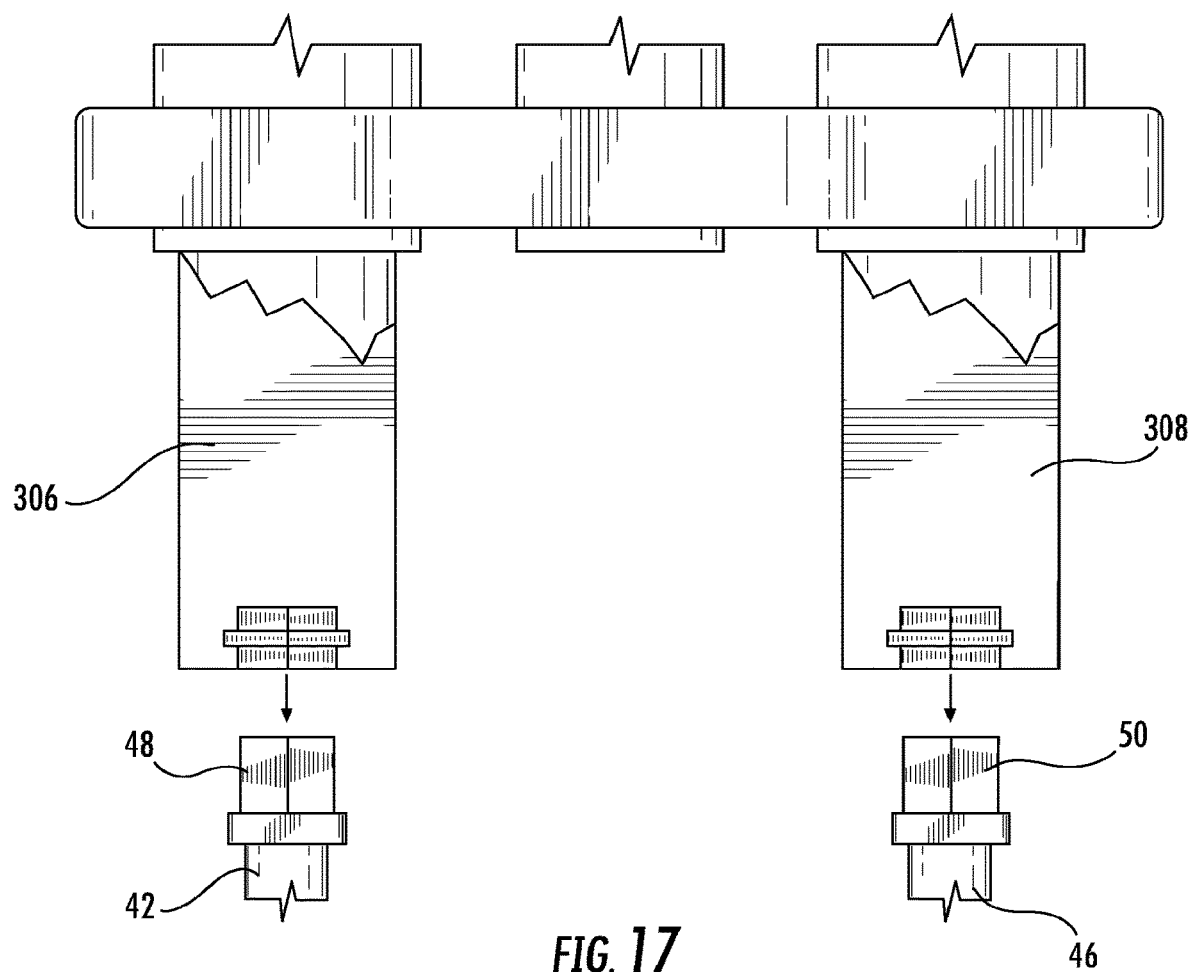
FIG. 17 is a view showing a manner of attachment of the operating tool to the drive shafts of the device.
Figure 18:
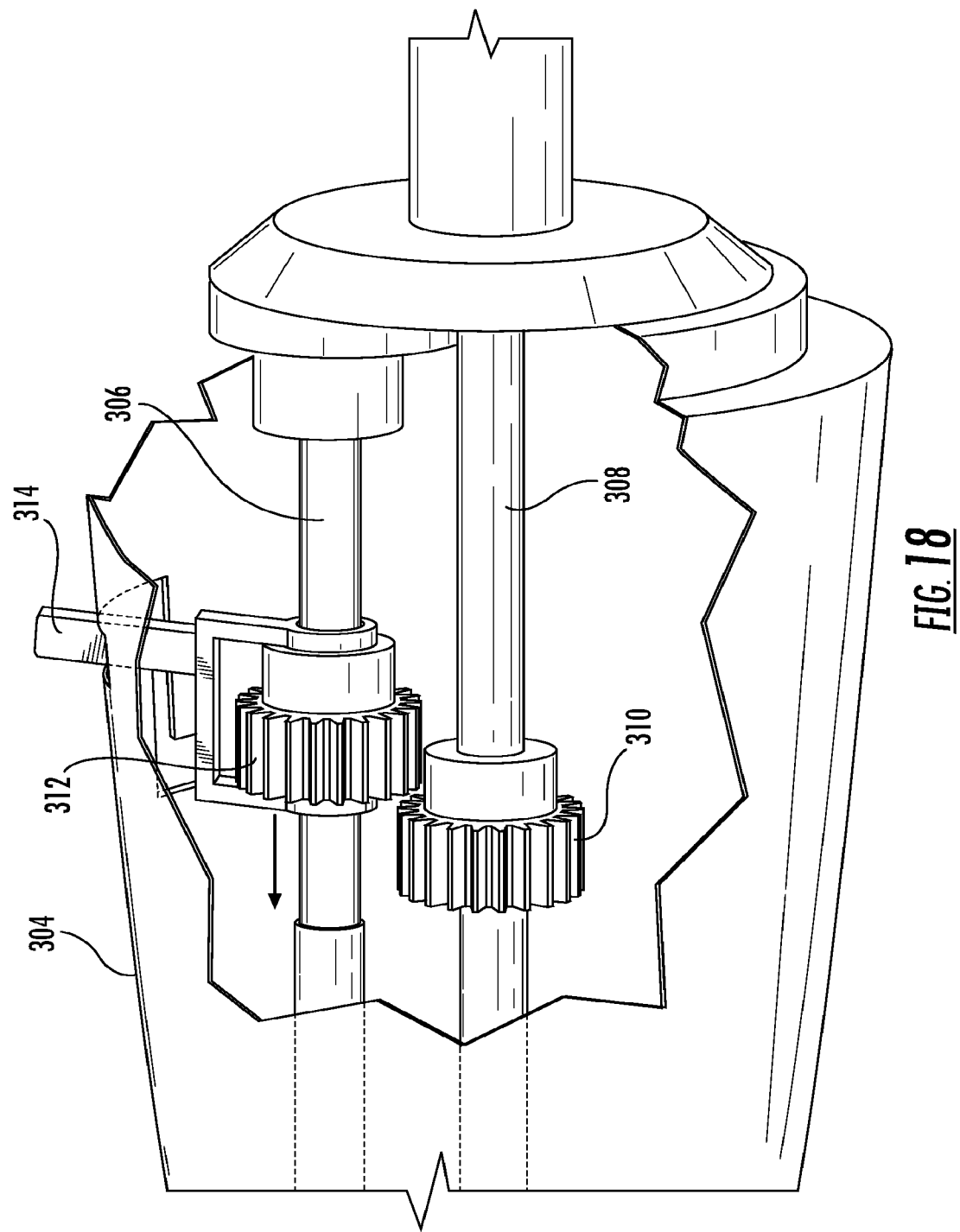
FIG. 18 is a breakaway perspective view of the handle of the operating tool.
Figure 19:
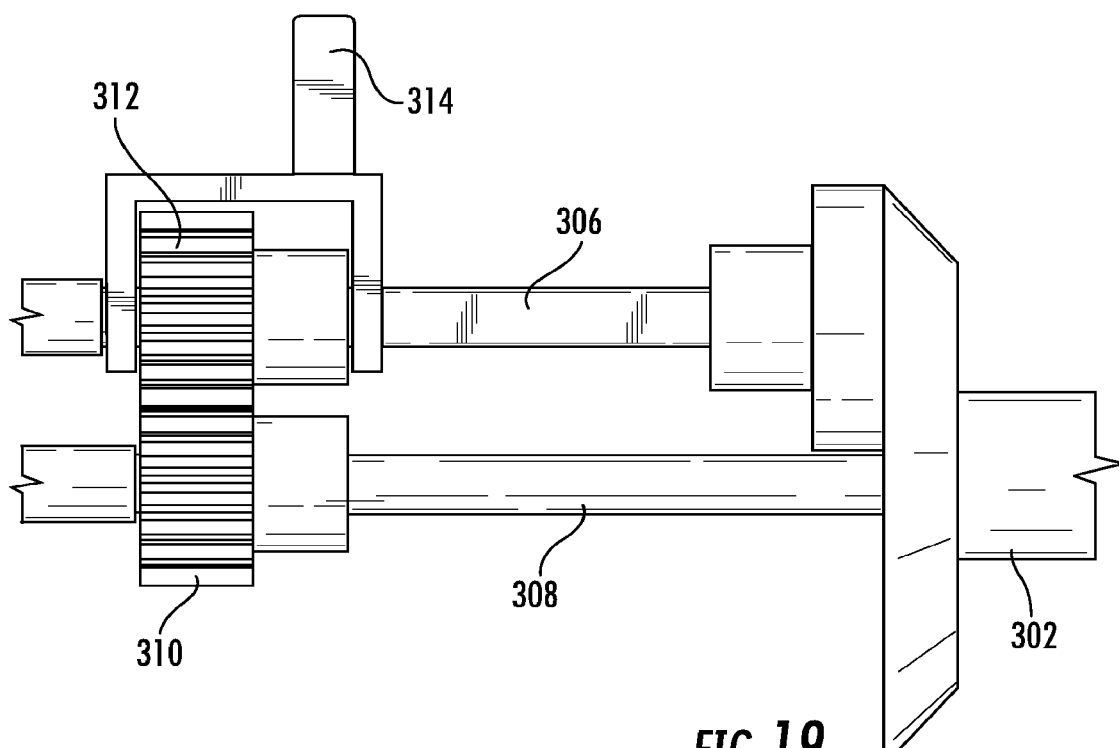
FIG. 19 is a perspective view of gears in the handle engaged for operation of both drive shafts.

The device is provided with a tool for operating the interbody fusion device as it is adjusted in situ in a patient's spine. The operating tool 300 is shown generally in FIG. 16 and comprises a handle member 302, a gear housing 304 and torque rod members 306 and 308. The torque rod members connect to the drive shafts of expandable shell 12. One embodiment for connecting the torque rod members to the drive shafts of expandable shell 12 is shown in FIG. 17. In this arrangement, ends 48 and 50 of drive shafts 42 and 46 can be provided with a hex-shaped head. The ends of torque rod members 306 and 308 can be provided with correspondingly shaped receivers for clamping around ends 48 and 50.

Figure 20:
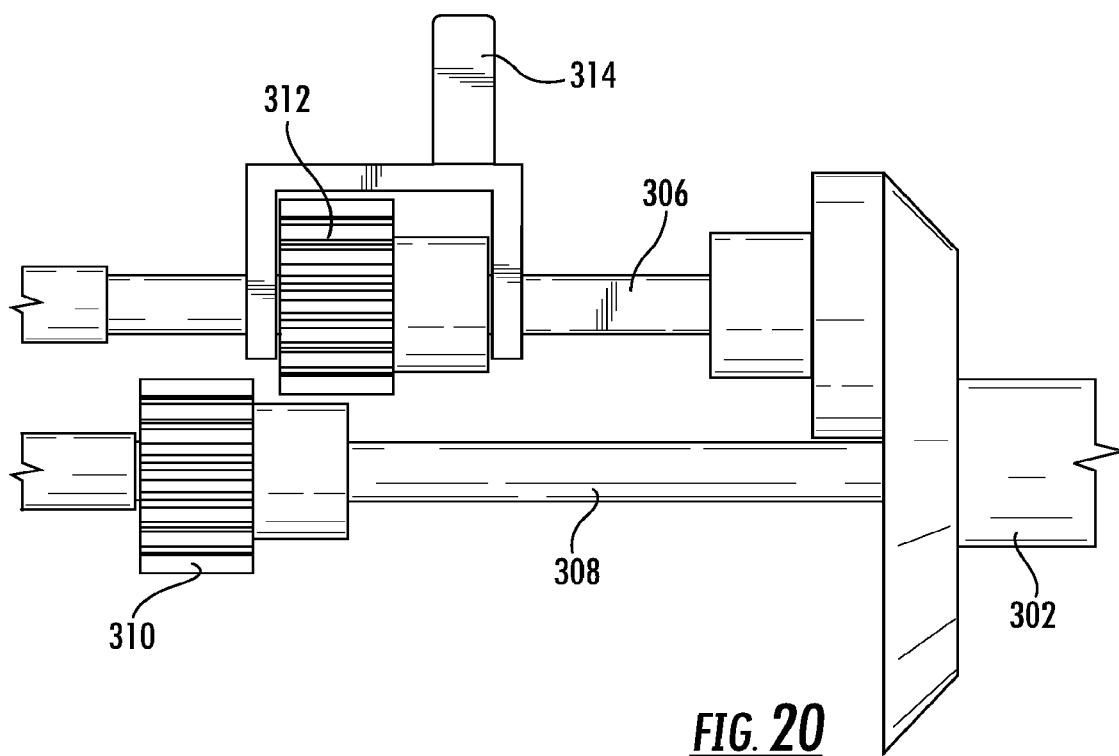
FIG. 20 is a perspective view of gears in the handle disengaged for operation of a single drive shaft.

Within the gear housing 304, handle member 302 directly drives torque rod member 308. Torque rod member 308 is provided with spur gear member 310 and torque rod member 306 is provided with spur gear member 312. Spur gear 312 is slidably received on torque rod member 306 and can move in and out of engagement with spur gear 310. Spur gear lever 314 engages with spur gear 312 for moving spur gear 312 into and out of engagement with spur gear 310. When torque rod member 308 is rotated by handle 302, and spur gear 312 is engaged with spur gear 310, rotation is translated to torque rod member 306. In this condition, torque rod member 308 rotates drive shaft 46 simultaneously with torque rod member 306 rotates drive shaft 42 to effect expansion of shell 12 as shown in FIGS. 7A-7C. Spur gear 312 can be moved out of engagement with spur gear 310 by retracting spur gear lever 314 as shown in FIG. 20. With spur gear 312 out of engagement with spur gear 310, rotation of handle 302 only turns torque rod member 310. In this condition, torque rod member 308 rotates drive shaft 46 solely and drive shaft 42 remains inactive to effect the tilt to the top member of shell 12 as shown in FIG. 8 and FIGS. 15A-15C to achieve lordosis.

To achieve expansion of the device in the described embodiment, the operator will turn handle member 302 clockwise to engage torquing. This applied torque will then engage the compound reverted spur gear train composed of spur gear members 310 and 312. This series of gears will then spin torque rod members 306 and 308 in opposite directions of each other. Torque rod member 310 (in alignment with handle member 302) will spin clockwise (to the right) and torque rod member 306 will spin counterclockwise (to the left). The torque rod members will then rotate the drive shafts of interbody fusion device 12 expanding it to the desired height.

To achieve lordosis the operator will move the spur gear lever 314 back towards handle member 302. By doing so spur gear 312 connected to torque rod member 306 is disengaged from the overall gear train, which in turn will disengage torque rod member 306. As a result, torque rod member 308 will be the only one engaged with the interbody fusion device 12. This will allow the operator to contract the posterior side of the implant device to create the desired degree of lordosis.

Although the invention has been disclosed with reference to various particular embodiments, it is understood that equivalents may be employed and substitutions made herein without departing from the scope of the invention.

Having thus described the preferred embodiment of the invention, what is claimed as new and desired to be protected by Letters Patent includes the following:

1. A spinal implant device for placement between vertebral bodies, the device comprising:
   a housing;
   at least one screw member in the housing, the at least one screw member having a through-opening; and
   at least one drive shaft in the housing extending substantially from a first end to a second end of the housing, the at least one drive shaft passing through the through-opening in the at least one screw member; wherein
   the housing comprises a first shell member and a second shell member, at least the first shell member having at least one riser member for receiving the at least one screw member,
   the at least one drive shaft is operable to rotate the at least one screw member, whereby the at least one screw member rotates with and travels along the at least one drive shaft,
   the at least one screw member is engageable with the at least one riser member, the at least one screw member having a tapered configuration, whereby rotation of the at least one screw member increases a diameter of the at least one screw member at a point of engagement with the at least one riser member, causing the first shell member and second shell member to move relative to each other to effect expansion of the housing.

2. The spinal implant device of claim 1, whereby the housing can be contracted by reversing a direction of rotation of the at least one screw member from that for expansion, decreasing the diameter of the screw member at the point of engagement with the at least one riser member.

3. The spinal implant device of claim 1, wherein the at least one riser member comprises a series of riser members of successively greater heights.

4. The spinal implant device of claim 3, whereby the at least one screw member is engageable with at least two successive riser members of the series of riser members at a time.

5. The spinal implant device of claim 4, whereby the series of riser members has gaps between individual riser members of the series of riser members, whereby the at least one screw member has a helical thread which can be received in the gaps.

6. The spinal implant device of claim 5, whereby rotation of the at least one screw member causes the at least one screw member to travel along the series of riser members, whereby rotation of the at least one screw member increases the diameter of the at least one screw member at the point of engagement with the at least one riser member, causing at least the first shell member and the second shell member to move relative to each other to effect expansion of the housing.

7. The spinal implant device of claim 6, whereby the housing can be contracted by reversing the direction of rotation of the at least one screw member from that for expansion, decreasing the diameter of the at least one screw member at the point of engagement with each successive riser member, and causing the at least one screw member to travel in reverse on the series of riser members of successively greater heights.

8. The spinal implant device of claim 7, wherein the at least one riser member of the first shell member comprises the series of riser members of successively greater heights and a second series of riser members of successively greater heights, whereby the at least one screw member comprises a first screw member and a second screw member, whereby the series of riser members receives the first screw member and the second series of riser members receives the second screw member.

9. The spinal implant device of claim 8, wherein each of the first and second screw members have a through opening configured to allow the at least one drive shaft to pass through and operably engage with the first and second screw members, whereby the first and second screw members are disposed such that a directional orientation of the helical thread of the first screw member is opposite to a directional orientation of the helical thread of the second screw member, whereby the first and second screw members move in opposite directions relative to each other upon rotation of the at least one drive shaft.

10. The spinal implant device of claim 8, further comprising a thrust bearing member engageable with the first and second drive shafts to limit axial movement of the first and second drive shafts.

11. The spinal implant device of claim 10, further comprising a locking member engageable with the first and second drive shafts to selectively prevent rotation of the first and second drive shafts.

12. The spinal implant device of claim 1, further comprising a thrust bearing member engageable with the at least one drive shaft to prevent axial movement of the at least on drive shaft.

13. The spinal implant device of claim 12, further comprising a locking member engageable with the at least one drive shaft to selectively prevent rotation of the at least one drive shaft.

14. A spinal implant device for placement between vertebral bodies, the device comprising:
a housing;
at least one screw member in the housing; and
at least one drive shaft; wherein
the housing comprises a first shell member and a second shell member, at least the first shell member having a plurality of riser members for receiving the at least one screw member,
the at least one drive shaft is operable to rotate the at least one screw member,
the at least one screw member is engageable with the plurality of riser members, the at least one screw member having a tapered configuration, whereby rotation of the at least one screw member increases a diameter of the at least one screw member at a point of engagement with the plurality of riser members, causing the first shell member and second shell member to move relative to each other to effect expansion of the housing,
wherein the second shell member having a plurality of riser members for receiving the at least one screw member, the plurality of riser members of the first shell member have gaps between riser members, the plurality of riser members of the second shell member have gaps between riser members, wherein the gaps of the first shell member each have a position corresponding to positions of riser members of the second shell member and vice versa, thereby permitting the plurality of riser members of the first shell member and the plurality of riser members of the second shell member to intermesh.

15. The spinal implant device of claim 14, whereby the at least one screw member is simultaneously engageable with at least two successive riser members of the plurality of riser members on the first shell member and at least two successive riser members of the plurality of riser members on the second shell member, whereby rotation of the at least one screw member causes the at least one screw member to travel simultaneously along the plurality of riser members on the first shell member and the plurality of riser members on the second shell member, where rotation of the at least one screw member increases the diameter of the at least one screw member at points of engagement with each successive riser member, causing the first shell member and the second shell member to move relative to each other to effect expansion of the housing.

16. A spinal implant device for placement between vertebral bodies, the device comprising:
a housing;
a plurality of screw members in the housing the plurality of screw members comprising at least one first screw member positioned along a first lateral area of the housing, and at least one second screw member positioned along a second lateral area of the housing, the at least one first and second screw members each having a through-opening;
a first drive shaft and a second drive shaft, the first and the second drive shafts extending substantially from a first end to a second end of the housing, the first drive shaft passing through the through-opening in the at least one first screw member, and the second drive shaft passing through the through-opening in the at least one second screw member; wherein
the housing comprises a first shell member and a second shell member, at least the first shell member having at least one first riser member for receiving the at least one first screw member, and having at least one second riser member for receiving the at least one second screw member,
the first drive shaft, positioned along the first lateral area of the housing, is operable to rotate the at least one first screw member whereby the at least one first screw member rotates with and travels along the first drive shaft, the second drive shaft, positioned along the second lateral area of the housing, is operable to rotate the at least one second screw member whereby the at least one second screw member rotates with and travels along the second drive shaft, the first drive shaft and second drive shaft being operable independently of each other,
the at least one first screw member is engageable with the at least one first riser member, the at least one second screw member is engageable with the at least one second riser member, the plurality of screw members each having tapered configurations, whereby rotation of a screw member of the plurality of screw members increases a diameter of that screw member at a point of engagement with a riser member of the at least one first riser member or a riser member of the at least one second riser member, causing the first shell member and second shell member to move relative to each other to effect expansion of the housing, whereby contraction of the housing can be effected from reversing a direction of rotation of that screw member from that for expansion, decreasing the diameter of that screw member at the point of engagement with the riser member, wherein a degree of expansion or contraction of the first lateral area of the housing is independently adjustable relative to a degree of expansion or contraction of the second lateral area of the housing when the at least one first screw member and the at least one second screw member are independently adjusted to different degrees of rotation.

17. The spinal implant device of claim 16, wherein the at least one first riser member comprises a first series of riser members and the at least one second riser member comprises a second series of riser members, each series comprising riser members of successively greater heights, each series of riser members is for receiving one screw member of the plurality of screw members, whereby rotation of a screw member of the plurality of screw members causes that screw member to travel along a respective one of the series of riser members of successively greater heights.

18. The spinal implant device of claim 17, whereby the at least one first screw member comprises a first pair of screw members and the at least one second screw member comprises a second pair of screw members.

19. The spinal implant device of claim 18, wherein the first pair of screw members are disposed such that a directional orientation of the helical thread of a first screw member of the first pair is opposite to a directional orientation of a second screw member of the first pair, whereby the first and second screw members of the first pair move in opposite directions relative to each other along the first lateral area of the housing upon rotation of the first drive shaft engaging the first pair of screw members, wherein the second pair of screw members are disposed such that a directional orientation of the helical thread of a first screw member of the second pair is opposite to a directional orientation of the helical thread of a second screw member of the second pair, whereby the first and second screw members of the second pair move in an opposite direction relative to each other along the second lateral area of the housing upon rotation of the second drive shaft engaging the second pair of screw members.

20. The spinal implant device of claim 19, wherein the first and second pairs of screw members are disposed such that when the first drive shaft is rotated in a first direction the first pair of screw members move distally from the central portion of the first lateral area of the housing, and when the second drive shaft is rotated in a second direction opposite to the first direction the second pair of screw members move distally from the central portion of the second lateral area of the housing.

21. The spinal implant device of claim 16, wherein
the at least one first riser member of the first shell member comprises a plurality of first riser members, the at least one second riser member of the first shell member comprises a plurality of second riser members, and the second shell member comprises a plurality of first riser members and a plurality of second riser members,
the plurality of first riser members of the first shell member have gaps between riser members, the plurality of first riser members of the second shell member have gaps between riser members, wherein the gaps between the first riser members of the first shell member each have a position corresponding to positions of the first riser members of the second shell member and vice versa, thereby permitting the plurality of first riser members of the first shell member and the plurality of first riser members of the second shell member to intermesh, and
the plurality of second riser members of the first shell member have gaps between riser members, the plurality of second riser members of the second shell member have gaps between riser members, wherein the gaps between the second riser members of the first shell member each have a position corresponding to positions of the second riser members of the second shell member and vice versa, thereby permitting the plurality of second riser members of the first shell member and the plurality of second riser members of the second shell member to intermesh.

\* \* \* \* \*